US007067283B2

(12) United States Patent
Weinrich et al.

(10) Patent No.: US 7,067,283 B2
(45) Date of Patent: Jun. 27, 2006

(54) PRODUCING TELOMERASE ACTIVATORS AND INHIBITORS BY SCREENING WITH PURIFIED TELOMERASE

(75) Inventors: Scott L. Weinrich, Chesterfield, MO (US); Edward M. Atkinson, III, Seattle, WA (US); Serge P. Lichtsteiner, Encinitas, CA (US); Alain P. Vasserot, Berkeley, CA (US); Ronald A. Pruzan, Palo Alto, CA (US)

(73) Assignee: Geron Corporation, Menlo Park, CA (US)

( * ) Notice: Subject to any disclaimer, the term of this patent is extended or adjusted under 35 U.S.C. 154(b) by 0 days.

(21) Appl. No.: 10/811,033

(22) Filed: Mar. 26, 2004

(65) Prior Publication Data

US 2005/0089883 A1  Apr. 28, 2005

Related U.S. Application Data

(63) Continuation of application No. 10/330,872, filed on Dec. 24, 2002, now Pat. No. 6,787,133, which is a continuation of application No. 09/717,828, filed on Nov. 20, 2000, now Pat. No. 6,517,834, which is a continuation-in-part of application No. 09/420,056, filed on Oct. 18, 1999, now Pat. No. 6,261,556, which is a continuation of application No. 08/833,377, filed on Apr. 4, 1997, now Pat. No. 5,968,506, which is a continuation-in-part of application No. 08/510,736, filed on Aug. 4, 1995, now abandoned.

(51) Int. Cl.
*C12Q 1/42* (2006.01)
*C12Q 1/68* (2006.01)

(52) U.S. Cl. .................. 435/69.2; 435/14; 435/194; 435/252.3; 435/320.1; 536/23.2

(58) Field of Classification Search ............... 424/94.5; 435/14, 194, 252.3, 320.1, 6, 8, 9, 91.3, 69.2; 536/23.2; 432/412, 413
See application file for complete search history.

(56) References Cited

U.S. PATENT DOCUMENTS

| 5,489,508 | A | 2/1996 | West et al. ................... 435/6 |
| 5,583,016 | A | 12/1996 | Villeponteau et al. ...... 435/91.3 |
| 5,639,613 | A | 6/1997 | Shay et al. ................... 435/6 |
| 5,698,686 | A | 12/1997 | Gottschling et al. ....... 536/23.1 |
| 5,747,317 | A | 5/1998 | Cao .......................... 435/194 |
| 5,770,422 | A | 6/1998 | Collins ...................... 435/194 |
| 5,858,777 | A | 1/1999 | Villeponteau et al. ...... 435/325 |
| 5,888,747 | A | 3/1999 | Cao .......................... 435/7.1 |
| 5,916,752 | A | 6/1999 | Gottschling et al. ........... 735/6 |
| 5,917,025 | A | 6/1999 | Collins ...................... 536/23.2 |
| 6,093,809 | A | 7/2000 | Cech et al. ................ 536/23.5 |
| 6,517,834 | B1 * | 2/2003 | Weinrich et al. .......... 424/94.5 |
| 6,787,133 | B1 * | 9/2004 | Weinrich et al. .......... 424/94.5 |

FOREIGN PATENT DOCUMENTS

| WO | WO 94/03205 | 2/1994 |
| WO | WO 95/13382 | 5/1995 |
| WO | WO 96/01614 | 1/1996 |
| WO | WO 96/01825 | 1/1996 |
| WO | WO 96/01835 | 1/1996 |
| WO | WO 96/12811 | 5/1996 |
| WO | WO 96/19580 | 6/1996 |
| WO | WO 96/40868 | 12/1996 |
| WO | WO 98/14593 | 4/1998 |
| WO | WO 98/45450 | 10/1998 |

OTHER PUBLICATIONS

Blackburn, E.H., "Telomerases", Annu. Rev. Biochem, 61:113-29 (1992).
Blackburn, E.H., et al., "A Conserved Secondary Structure for Telomerase RNA", Cell, 67:343-353 (1991).
Blackburn, E.H., et al., "Telomeres", TIBS, 16:378-381 (1991).
Bochnig, P., et al., "A Monoclonal Antibody Against 2,2,7-trimethylguanosine that Reacts with Intact Class U, Small, Nuclear Ribonucleoproteins as well as with 7-Methyl-Guanosine-Capped RNAs", Eur. J. Biochem., 168:461-476 (1987).
Counter, et al., "Telomerase Activity in Human Ovarian Carcinoma", Proc. Natl. Acad. Sci. USA, 91:2900-2904 (1994).
Feng, J., et al., "The RNA Component of Human Telomerase", Sci., 269(5228):1236-1241 (1995).
Graham, et al., "Characteristics of Human Cell Line Transformed by DNA from Human Adenovirus Type 5", J. Gen. Virol., 26:59-77 (1977).
Harley, C.B., "Telomere Loss: Mitotic Clock or Genetic Time Bomb?", Mutation Res., 256:271-282 (1991).

(Continued)

*Primary Examiner*—Tekchand Saidha
(74) *Attorney, Agent, or Firm*—J. Michael Schiff; David J. Earp

(57) ABSTRACT

This invention provides purified telomerase and methods of purifying it. The methods involve the use of several sequential steps, including the use of matrices that bind molecules bearing negative charges, matrices that bind molecules bearing positive charges, intermediate-selectivity matrices, methods that separate molecules based on their size, shape, or buoyant density, and by affinity purification.

25 Claims, 7 Drawing Sheets

OTHER PUBLICATIONS

Lingner, J., et al., "Purification of Telomerase from Euplotes Aediculatus: Requirement of a Primer 3' Overhang", Proc. Natl. Acad. Sci. USA, 93:10712-10717 (1996).

Lingner, J., et al., "Telomerase RNAs of Different Ciliates Have a Common Secondary Structure and a Permuted Template", Genes and Devel., 8:1984-1988 (1994).

Miller, et al., "Improved Retroviral Vectors for Gene Transfer and Expression", Biotechniques, 7:980-990 (1992).

Morin, G., "The Human Telomere Terminal Transferase Enzyme is a Ribonucleoprotein that Synthesizes TTAGGG Repeats", Cell, 59:521-529 (1989).

Nakamura, T., et al., "Telomerase Catalytic Subunit Homologs from Fisson Yeast and Human", Science, 277:955-959, (1997).

Nomura, N., et al., "Prediction of the Coding Sequences of Unidentified Human Genes", DNA Res., 1:27-35 (1994).

Nomura, N., et al., Accession D21163 Genbank Sequence.

Schnapp, et al., "One Step Affinity Purification Protocol for Human Telomerase", Nucleic Acids Res., 26(13):3311-3313 (1998).

Singer, M., et al, "TLC1: Template RNA Component of *Saccharomyces cerevisiae* Telomerase", Science, 266:404-409 (1994).

Srivastava, M., et al., "Genomic Organization and Chromosomal Localization of the Human Nucleolin Gene", Jour. Of Bio. Chem., 265(25):14922-14931 (1990).

Stillman, et al., "Replication and Supercoiling of Simian Virus 40 DAN in Cell Extracts from Human Cells", Mol. And Cell Bio., 5:2051-2060 (1985).

Villeponteau, B., et al., "Mammalian Telomerase", U.S. Appl. No. 09/060,253, filed Apr. 14, 1998.

Derwent Summary of JP 07 242 566A, "An Immunosuppressant Contg. Human Nucleolin Antibody—Is Effective Against Autoimmune Disease".

Derwent Summary of JP 9154575A, "Telomerase Useful in Diagnosis of Tumours—Comprises RNA Protein Having Aggregate Containing Protein Located At Terminal Region of Human Chromosone".

"Characterization and Expression of Human Telomerase", Ph.D. Thesis by Ariel Athena Avilion, State University of New York at Stony Brook, dated May 1995.

* cited by examiner

SEQUENCE LISTING

<160> NUMBER OF SEQ ID NOS: 11

<210> SEQ ID NO 1
<211> LENGTH: 31
<212> TYPE: DNA
<213> ORGANISM: Homo sapiens

<400> SEQUENCE: 1
gcctacgccc ttctcagtta gggttagaca a                              31

<210> SEQ ID NO 2
<211> LENGTH: 22
<212> TYPE: DNA
<213> ORGANISM: Homo sapiens

<400> SEQUENCE: 2
cgcccttctc agttagggtt ag                                         22

<210> SEQ ID NO 3
<211> LENGTH: 30
<212> TYPE: DNA
<213> ORGANISM: Homo sapiens

<400> SEQUENCE: 3
gccgagtcct gggtgcacgt cccatagctc                                 30

<210> SEQ ID NO 4
<211> LENGTH: 30
<212> TYPE: DNA
<213> ORGANISM: Homo sapiens

<400> SEQUENCE: 4
gaacgggcca gcagctgaca tttttttgttt                                30

<210> SEQ ID NO 5
<211> LENGTH: 30

-continued

<210> SEQ ID NO 5
<211> LENGTH: 30
<212> TYPE: DNA
<213> ORGANISM: Homo sapiens

<400> SEQUENCE: 5
gctctagaat gaacggtgga aggcggcagg                               30

<210> SEQ ID NO 6
<211> LENGTH: 18
<212> TYPE: DNA
<213> ORGANISM: Homo sapiens

<400> SEQUENCE: 6
ttagggttag ggttaggg                                            18

<210> SEQ ID NO 7
<211> LENGTH: 18
<212> TYPE: DNA
<213> ORGANISM: Homo sapiens

<400> SEQUENCE: 7
ccctaaccct aaccctaa                                            18

<210> SEQ ID NO 8
<211> LENGTH: 18
<212> TYPE: DNA
<213> ORGANISM: Homo sapiens

<400> SEQUENCE: 8
aatccgtcga gcagagtt                                            18

<210> SEQ ID NO 9
<211> LENGTH: 28
<212> TYPE: PRT
<213> ORGANISM: Homo sapiens

<400> SEQUENCE: 9

Cys Arg Lys Lys Thr Met Phe Arg Tyr Leu Ser Val Thr Asn Lys Gln
1               5                   10                  15

Lys Trp Asp Gln Thr Lys Lys Arg Lys Glu Asn
            20                  25

<210> SEQ ID NO 10
<211> LENGTH: 24
<212> TYPE: PRT
<213> ORGANISM: Homo sapiens

<400> SEQUENCE: 10

Cys His Ile Ser Glu Pro Lys Glu Arg Val Tyr Lys Ile Leu Gly Lys
1               5                   10                  15

Lys Tyr Pro Lys Thr Glu Glu Glu
            20

<210> SEQ ID NO 11
<211> LENGTH: 22
<212> TYPE: PRT
<213> ORGANISM: Homo sapiens

<400> SEQUENCE: 11

Asp Asn Asn Leu Cys Ile Leu Ala Leu Leu Arg Phe Leu Leu Ser Leu
1               5                   10                  15

Glu Arg Phe Asn Ile Leu
            20

US 7,067,283 B2

PRODUCING TELOMERASE ACTIVATORS AND INHIBITORS BY SCREENING WITH PURIFIED TELOMERASE

REFERENCE TO RELATED APPLICATIONS

This application is a continuation of 10/330,872, filed Dec. 24, 2002 (issued as U.S. Pat. No. 6,787,133 on Sep. 7, 2004); which is a continuation of U.S. Ser. No. 09/717,828, filed Nov. 20, 2000 (issued as U.S. Pat. No. 6,517,834 on Feb. 11,2003); which is a continuation-in-part of U.S. Ser. No. 09/420,056, filed Oct. 18, 1999 (issued as U.S. Pat. No. 6,261,556 on Jul. 17, 2001); which is a continuation of U.S. Ser. No. 08/833,377, filed Apr. 4, 1997 (issued as U.S. Pat. No. 5,968,506 on Oct. 19, 1999); which is continuation-in-part of U.S. Ser. No. 08/510,736; filed Aug. 4, 1995 (abandoned).

BACKGROUND OF THE INVENTION

The American population is aging. The fastest growing segment of the population is persons over 85 years of age, who are expected to number over 30 million by the year 2040. This demographic surge is creating significant needs for drugs for the treatment of age-related diseases and has led to increased interest in the aging process and diseases associated with it, including cancer.

Organisms age, in part, because their cells have a finite capacity to continue dividing. As they reach that limit, cells become senescent. Cell senescence has been traced to the ends of a cell's chromosomes, the telomeres. With each cell division, the telomeres lose some DNA and become shorter. At some point this shortening becomes critical. Cells sense this and arrest chromosome replication to avoid further loss. Hence, the cell is no longer able to divide.

Not all cells become senescent. Single-cell organisms and certain mammalian cells have no fixed cell division limit. Investigators have discovered that many of these cells contain a ribonucleoprotein enzyme called telomerase. Telomerase replaces the DNA that is usually lost from the telomeres during cell division. (E. H. Blackburn, Annu. Rev. Biochem. 1992, 61:113–29.) Consequently, the telomeres never shorten past the critical length and the cells never reach senescence.

Particularly interesting, investigators have found that the cells of many human cancers have telomerase. (C. B. Harley, Mutation Research 1991 256:271–282.) This helps explain why cancer cells continue dividing without becoming senescent. It also suggests a potent weapon in the battle against cancer: If telomerase activity in cancer cells can be inhibited, the cancer cells are expected to reach senescence and cease dividing.

Developing methods to regulate telomerase activity requires sources of purified telomerase and, in particular, purified human telomerase. Purified telomerase would be useful in developing and testing assays for measuring telomerase activity, for example, to evaluate the assay and for use as a standard in the assay. Assays for telomerase are useful in characterizing cancer cells or pre-cancer cells, because most cancer cells express telomerase. Purified telomerase would be more useful than crude telomerase preparations to identify and test regulators, inhibitors or activators of telomerase activity in vitro assays. Moreover, purified telomerase would facilitate a thorough biochemical analysis of the enzyme's mechanism, which may provide insight for development of mechanism-based regulators. Purified telomerase also would be useful in the preparation of antibodies against telomerase. Such antibodies would in turn be especially useful as reagents to purify human telomerase and may be useful in cancer diagnosis or prognosis. Purified telomerase also will help provide amino acid sequence information useful in cloning the various components of the ribonucleoprotein.

While there is a need for purified telomerase, the purification of the human enzyme has posed technical challenges. Telomerase is a rare ribonucleoprotein expressed in human cells only in very low abundance. It has been estimated that human cells known to express the highest levels of telomerase activity may have only about one hundred molecules of the enzyme per cell. The fact that telomerase is a complex, multi-component structure further impedes its purification. Human cells also possess comparatively very high levels of non-telomerase ribonucleoproteins. These other ribonucleoproteins might have chromatographic purification properties similar to the telomerase ribonucleoprotein, which makes purification of telomerase from human cells difficult. Thus, there is a need for purified telomerase and purified human telomerase, in particular.

DESCRIPTION OF THE INVENTION

Figure 1:
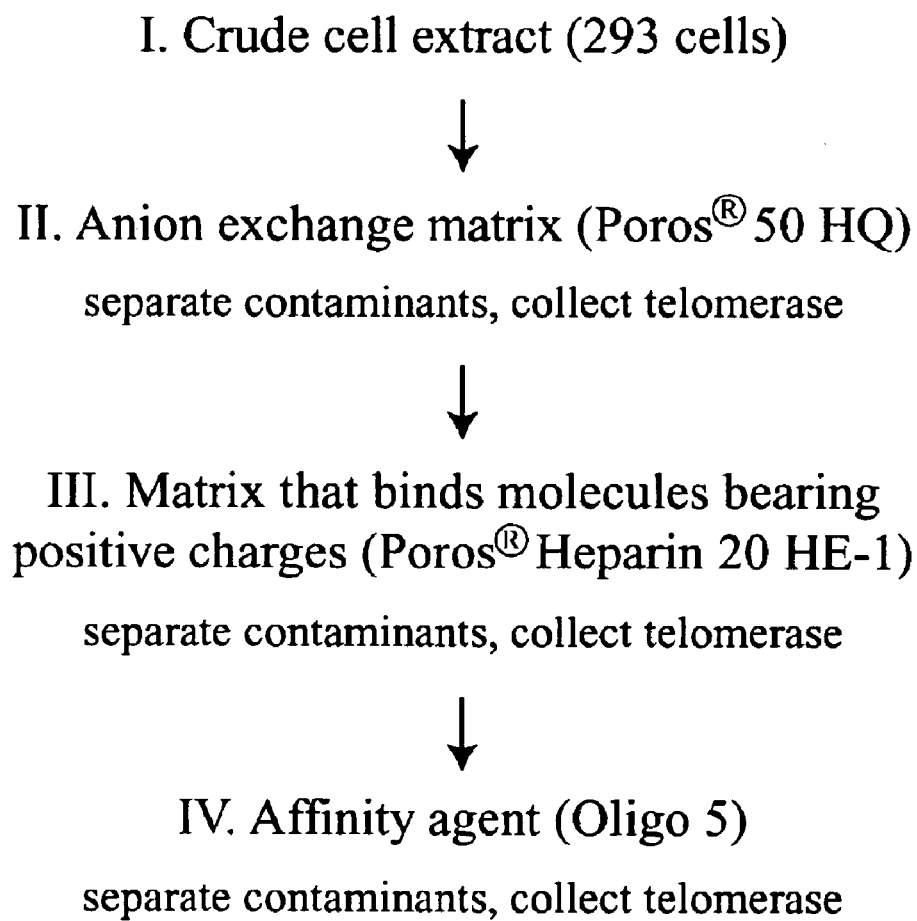
FIG. 1 depicts a four-step protocol for purifying telomerase.

This invention provides purified telomerase and methods of making it.

As used herein, the term "telomerase" refers to a ribonucleoprotein enzyme of eukaryotic origin identifiable by its ability to polymerize a DNA sequence of a eukaryotic telomere. Telomerase is further characterized by having an RNA component having sequences complementary to at least part of the telomeric repeat of the source species and having one or more protein components. As used herein, "human telomerase" refers to telomerases naturally found in human cells or having the same amino acid and nucleotide sequences, just as "mammalian telomerase" refers to the class of telomerases naturally found in mammalian cells or having the same amino acid and nucleotide sequences as the natural forms. Human telomerase contains the RNA component hTR. Telomerases include all allelic forms of telomerase, including wild-type and mutant forms.

This invention provides purified telomerase isolated from any cells expressing telomerase, for example, crude extracts of normal cells, cancer cells, immortalized cells, human or animal tissues, tumors, or from cells expressing telomerase recombinantly.

As used herein, the term "purified telomerase" means telomerase preparations having at least 2000-fold increased relative purity. As used herein, a telomerase preparation has 2000-fold increased relative purity if the specific activity of telomerase in the preparation is at least 2000 times greater than the specific activity of telomerase of crude extracts of suspension-capable 293 cells, described herein below, and as measured by the primer elongation assay described herein below in Example I.A.

This invention also provides telomerase preparations having at least 3000-fold increased relative purity, at least 20,000-fold increased relative purity, at least 60,000-fold increased relative purity, at least 100,000-fold increased relative purity.

Methods of purifying telomerase can involve determining the presence or amount of telomerase activity in a preparation. Several assays are available for this. As stated above, for the purpose of determining relative purity, the most preferred method of measuring the specific activity of telomerase is the primer elongation assay. This assay is described in Example I.A, below. Briefly, this assay measures the amount of radioactive nucleotides incorporated into polynucleotides synthesized on a primer sequence. The amount incorporated is measured as a function of the intensity of a band on a phosphoimager screen exposed to a gel on which the radioactive products are separated. A test experiment and a control experiment can be compared by eye on phosphoimager screens. This assay is based on an assay described by Morin, G. G., Cell 59:521–529, 1989.

Another assay for telomerase activity is the dot blot assay. The dot blot assay is useful for routine screening because it has high throughput and hundreds of assays can be carried out in a single day with a good portion of the labor performed automatically. Results are available by the afternoon of the second day. The dot blot assay is most effective for comparing activity of samples at roughly the same level of purity and less effective for samples at different stages of purity. Therefore, it is not a preferred assay for determining relative purity. A protocol for the dot blot assay is provided in Example I.B.

Other assays involve detecting the presence of the RNA component of telomerase. The sequence of the RNA component of telomerase for several species is known. The sequence for the RNA component of human telomerase has been isolated and is referred to herein as hTR.

Reverse transcription PCR ("RT-PCR") is a useful assay for determining the amount of telomerase RNA because it is very sensitive. A protocol for an RT-PCR assay is provided in Example I.C. Other methods for specific RNA detection can be used, for instance, Northern Analysis. A protocol for a Northern Analysis is provided in Example I.D. The major limitation of using any of the hTR assays to detect telomerase is that the presence of hTR does not mean that active telomerase is present. For example, normal somatic cells and some fractions from partially purified telomerase have significant quantities of hTR but no detectable telomerase activity.

Another very sensitive assay for telomerase activity is the TRAP assay, described in International application WO 95/13381 of which are incorporated herein by reference.

This invention is directed, in part, to methods of making purified telomerase from an impure composition, i.e., a composition containing telomerase and other contaminating organic biomolecules. Beginning with an impure telomerase composition, the methods involve the following steps: purifying the telomerase with a matrix that binds molecules bearing a negative charge (preferably an anion exchange matrix); purifying the telomerase with a matrix that binds molecules bearing a positive charge (preferably a heparin-containing matrix); and purifying telomerase with an affinity agent (preferably an oligonucleotide complementary to the RNA component of telomerase labeled with biotin and isolated with matrix-bound streptavidin or derivatives thereof). See FIG. 1.

Figure 2:
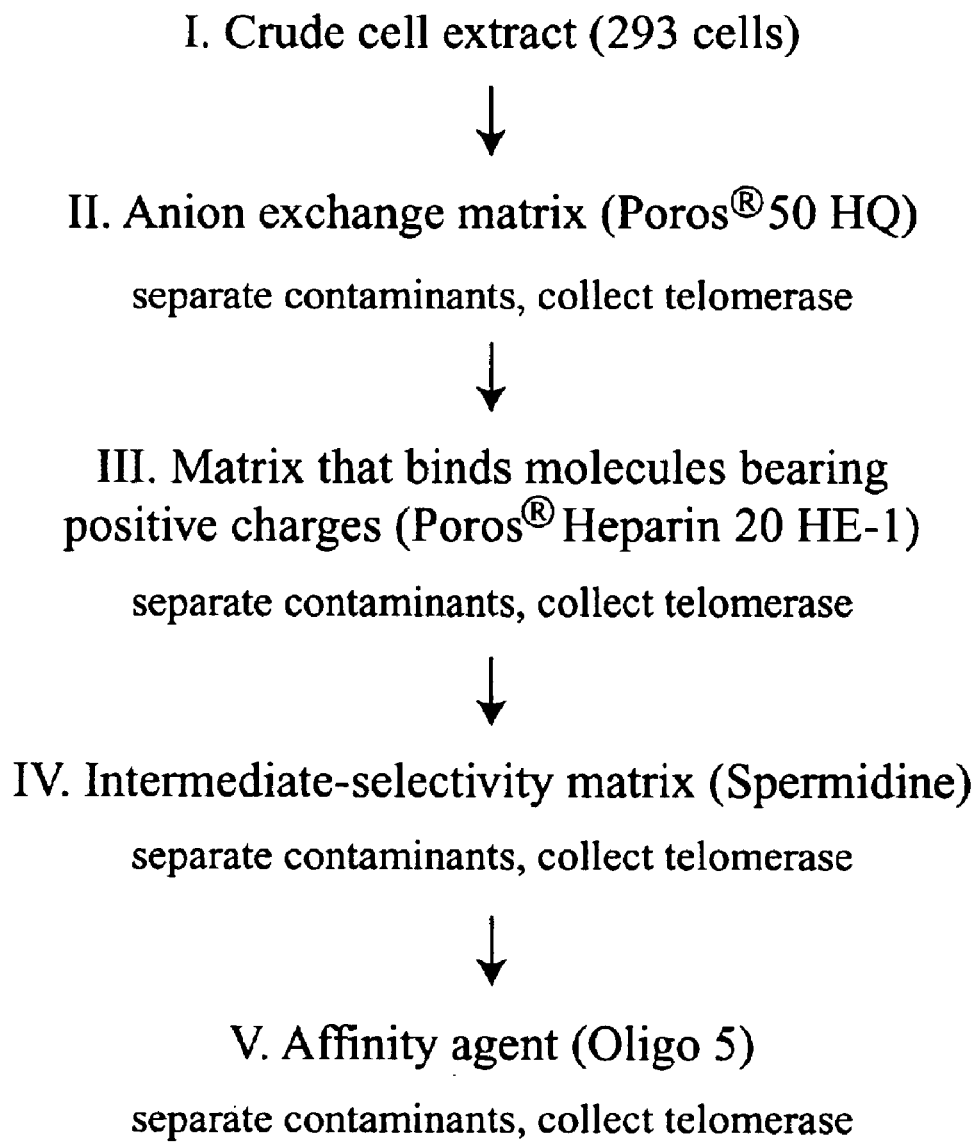
FIG. 2 depicts a five-step protocol for purifying telomerase.
Figure 3:
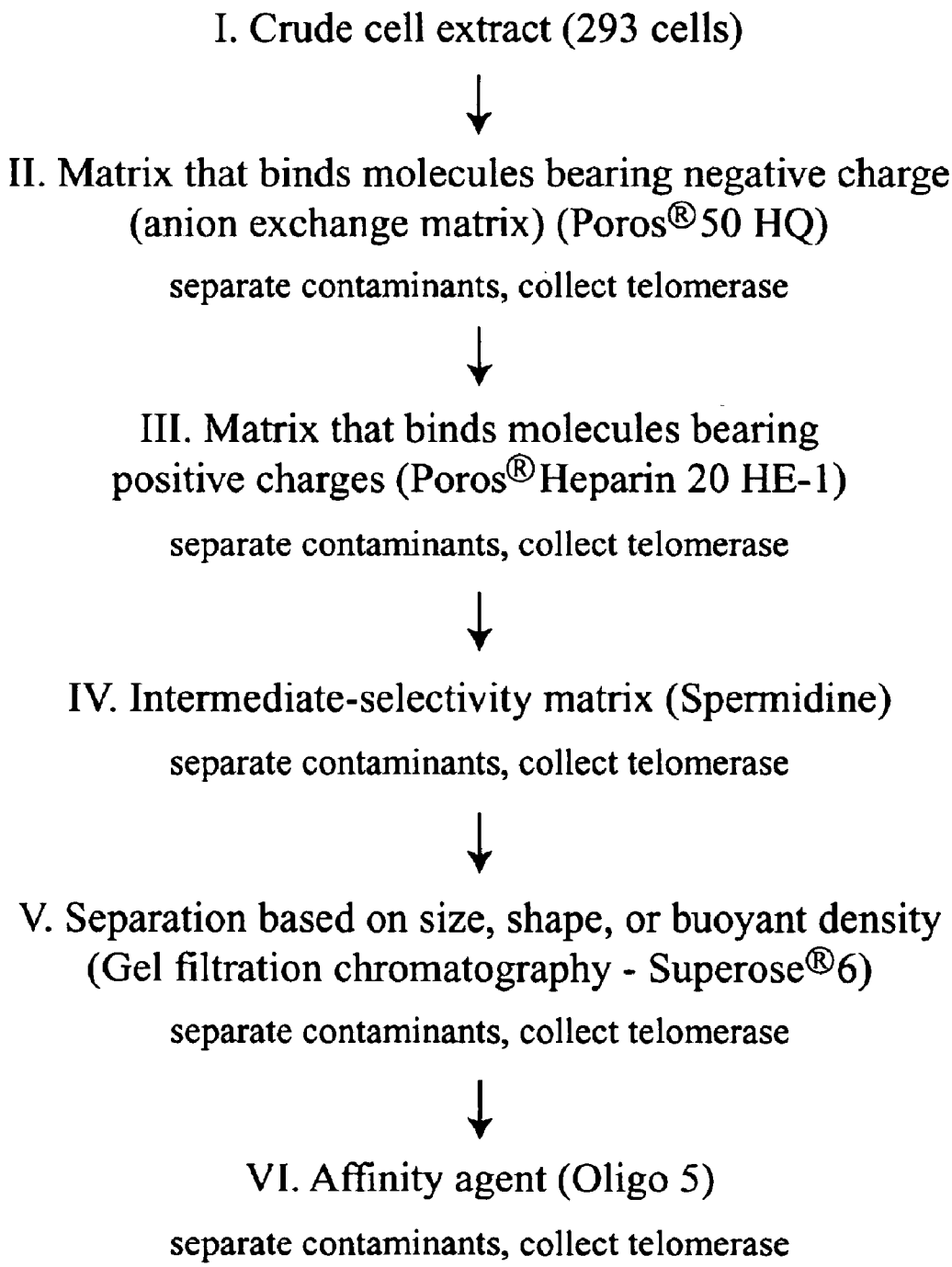
FIG. 3 depicts a six-step protocol for purifying telomerase.

Additional steps optionally can be included in the purification methods in order to produce telomerase preparations with higher relative purity. The telomerase can be further purified with an intermediate-selectivity resin (preferably a matrix containing spermidine) before affinity purification. See FIG. 2. The telomerase is further purified by methods that separate organic biomolecules according to molecular size, shape, or buoyant density (preferably gel filtration chromatography) before affinity chromatography. See FIG. 3.

The specific purification steps used and their sequence is at the discretion of the practitioner. However, the following guidance is provided. In general, it is preferred to begin with steps having high capacity and relatively low selectivity, followed by steps having intermediate capacity and/or selectivity, followed by steps having low capacity and high selectivity. Matrices binding molecules bearing positive or negative charges have high capacity and are useful as early steps because telomerase is present in low quantities in cells and purification methods typically will begin with large amounts of crude cell extract. Among these resins, purification with anion exchange resins are preferred first, followed by purification with resins that bind molecules bearing positive charges. The order can be reversed.

Purification steps having intermediate selectivity and capacity are preferred after high capacity steps. These include matrices of intermediate selectivity and separation based on molecular size, shape or buoyant density. While purification with intermediate selectivity resins is preferred first, the intermediate purification steps need not be limited to any particular order or number. In the four-step purification procedure described above, the intermediate steps are not included.

Specific affinity matrices have relatively low capacity, but high selectivity, and are preferred later in the purification process when telomerase is present with fewer contaminating materials. This step can be a sole purification step and is most useful when telomerase has at least 40-fold increased relative purity.

Purification of telomerase begins with an impure source composition, such as a crude cell extract, preferably rich in telomerase activity. Single-celled organisms with no limits on the number of cell divisions, such as Tetrahymena or yeast, more telomerase and are good sources for cell extract in the preparation of telomerase from such organisms. However, in multicellular organisms, especially mammals, not all cells make telomerase. Therefore, sources of cell extract have to be identified from the cell types available. In mammals, germ cells and tissue, cancer cells and tissue and immortalized cell lines are all sources of crude cell extract having telomerase activity. In rodents and possibly other non-primate mammals, some normal somatic tissues, e.g., mouse liver, are sources of crude cell extract having telomerase activity.

Immortalized cell lines are a particularly useful source of crude cell extract because they can be cultured and harvested in large quantities, thereby providing cell extract for large-scale telomerase preparations. In particular, in the preparation of purified human telomerase, 293 cells are preferred. 293 cells are of human embryonic kidney origin that have been transformed with fragments of adenovirus type 5 DNA (1977 Graham et al, J. Gen. Virol. 36:59–77). The cell line, which grows in monolayer cultures, was adapted to growth in suspension (1985 Stillman and Gluzman, Mol. and Cell Bio. 5:2051–2060). They are available from the ATCC (Accession No. ATCC CRL 1573).

The crude cell extract can be prepared in the typical manner. Generally, cells can be homogenized at about 4° C. in buffers at physiological pH. A more detailed protocol is provided in Example II. 293 cells are grown as suspension cultures in 8 liter spinner bottles in Joklik's—MEM, 5% newborn calf serum, 2 g/l NaHCO$_3$, 1% non-essential amino acids, 1% glutamine, 1% penicillin/streptomycin at 37° C. The cultures are maintained at 0.6×10$^6$ cells/mL and double every 24 hours. One also may contract with a cell culture specialist to culture large batches of cells. Contractors include Analytical Biological Systems (Wilmington, Del.), Cellex (Minneapolis, Minn.) and Berlex (South San Francisco, Calif.).

Other cell types, particularly those that grow readily in suspension cultures (which facilitates large scale culturing), also are useful for purifying human telomerase. Candidates include cell lines of B or T cell lineage, such as Namalwa (Burkitt's lymphoma), Daudi (Burkitt's lymphoma), Jarkat (acute T cell leukemia) and HUT 78 (cutaneous T cell lymphoma) lines. Also, HeLa cells (cervical carcinoma) have telomerase activity. Extracts from HeLa cells are available from Computer Cell Culture Center (Mons, Belgium).

The crude cell extract from mammalian cells used in the methods of this invention can be whole cell extract, but should include cytoplasmic extract. Nuclear extracts from 293 cells also have telomerase activity. For convenience, we have chosen cytoplasmic extracts as our source of human telomerase.

The amount of crude cell extract needed to purify telomerase depends, in part, upon the abundance of telomerase in the cell, the amount of telomerase lost at each step, and the ultimate degree of purification and amount desired. Example III describes the use of 128 liters of 293 cell suspension culture in a procedure that purified telomerase more than 3000-fold.

As purification advances, telomerase becomes both purer and more dilute. In this state, telomerase can be lost due to telomerase sticking to tubes, tubing, tips, etc. This loss can be minimized by the addition of detergent. In particular, the addition of up to about 0.1% Nonidet P-40 and about 1% Tween-20 (non-ionic detergents) does not inhibit telomerase activity, and can be added to all chromatography buffers.

A preferred step in a method for purifying telomerase from a crude cell extract involves contacting the telomerase with a matrix that binds molecules bearing negative charges, separating telomerase from other organic biomolecules that do not bind to the matrix and collecting the telomerase. Matrices binding molecules with a negative charge are useful in purifying telomerase because at pH between about 6 and about 9, the telomerase complex appears to have at least local negative charges. In a preferred embodiment of the invention the matrix is an anion exchange resin packed in a column. Anion exchange resins bind negatively charged molecules. One benefit of using anion exchange at this crude stage of preparation is the high binding capacity of these resins.

An isolating human telomerase, anion-exchange resins characterized by tertiary or quaternary amine functional groups provide the best results. POROS® 50 HQ (PerSeptive Biosystems, Cambridge, Mass.) is the preferred anion exchange resin. Super Q-650M (TosoHaas, Montgomeryville, Pa.) DEAE Sepharose® CL-6B (Pharmacia, Uppsala, Sweden) and Mono Q® (Pharmacia, Uppsala, Sweden) are also useful. In eluting fractions from the anion exchange resin, salt step elution is preferred. Also, linear salt gradient elution may be used to elute telomerase preferably using gradient volumes of less than ten column volumes.

A step preferred next in a method of purifying telomerase involves contacting the telomerase with a matrix that binds molecules bearing positive charges, separating telomerase from other organic biomolecules that do not bind to the column and collecting the telomerase. In a preferred embodiment the matrix comprises heparin. In particular, POROS® Heparin 20 HE-1 (PerSeptive Biosystems, Cambridge, Mass.) is useful as a matrix at this stage. Other useful matrices that bind molecules bearing positive charges include SP Sepharoseo CL-6B and Resource® S (Pharmacia, Uppsala, Sweden).

After the purification with high capacity matrices, telomerase can be purified by proceeding directly to affinity matrix purification, or through one or more intermediate purification steps.

In one intermediate purification step, the telomerase is contacted with hydroxyapatite, telomerase is separated from other organic biomolecules that do not bind to hydroxyapatite and the telomerase is collected. Hydroxyapatite is a crystalline form of calcium hydroxyphosphate which has the ability of bind proteins according to their basic or acidic character. Its basis of protein separation differs from that of simple ion exchange resins. Fractions may be eluted with buffers of different composition.

A preferred intermediate purification step involves contacting the telomerase with an intermediate-selectivity matrix; separating telomerase from other organic biomolecules that do not bind to the intermediate-selectivity matrix and collecting the telomerase. This step can be the fourth step of the five- or six-step purification schemes outlined in FIGS. 2 and 3. The main purpose of this step is to further purify the telomerase preparation before contacting it with an affinity agent. The types of matrices included at this step generally have lower binding capacities but can be more selective than ion exchange resins, thereby giving greater purification. They bind telomerase via interactions that are more complex than charge, alone, and are not as specific as, for example, antibodies. Binding characteristics can include, for example, combinations of electrostatic attraction, hydrophobic/hydrophilic attraction, affinity for particular components, such as nucleic acids or particular amino acids in the protein, affinity for chemical functional groups on molecules, and the variety of compounds known and used in protein purification for semi-specific separation of molecules. In particular, and without limitation, this invention contemplates the use of the following intermediate-selectivity matrices.

Matrices comprising a polyamine, such as spermidine or spermine are preferred in this step. These molecules contain primary and secondary amines amidst hydrocarbon chains. Both charge and hydrophobic interactions may be involved in binding telomerase.

Matrices comprising polynucleotides are useful in this step. In the case of human telomerase, polyguanylic acid retains telomerase activity. Without wishing to be bound by theory, these matrices are believed to be useful because telomerase is an enzyme that synthesizes DNA and contains an RNA moiety. Therefore, it is presumed to have domains which specifically bind polynucleotides.

Matrices comprising divalent metal ions are also useful in this step. Metals can be chelated on solid supports through molecules such as iminodiacetic acid or nitrilo-triacetic acid. Nickel is the most preferred metal and copper and zinc are also useful in purifying human telomerase. Without wishing to be limited by theory, metals are assumed to interact selectivity with specific amino acid residues in proteins. Histidine residues typically are involved in such interactions. Depending on the immobilized metal, only those proteins with sufficient local densities of histidines will be retained by the column. Some interactions between metals and proteins can be so strong that the protein cannot be recovered. Thus, each metal must be tested empirically for its utility in purification of a given protein. The binding of telomerase, as well as the release of telomerase must be efficient.

Matrices comprising positively charged proteinaceous substances also are useful in this step of the purification method. As used herein, proteinaceous substances include amino acids, poly-amino acids, peptides and proteins. Two positively charged materials, poly-L-lysine, and histone, selectivity retained human telomerase.

Matrices comprising aminophenyl-boronic acid also retain human telomerase. While not wishing to be limited by theory, the affinity of proteins for boronic acid is complicated but essentially involves interaction between diol groups on proteins with the immobilized acid.

In one embodiment of the invention, the telomerase is contacted sequentially with at least 2, at least 3 or at least 4 intermediate-selectivity matrices. Since contaminating proteins are unlikely to behave like telomerase on matrices having different characteristics, the use of more than one matrix improves the level of purification at this step. Sequences producing higher yields and purifications can be determined empirically, and matrices having higher capacity are preferred earlier in the sequence. Some combinations of two matrices in the series are not preferred due to their similar modes of separation, for example, one divalent metal column followed by another, spermine followed by spermidine, poly-L-lysine followed by histone.

Another intermediate purification step in a method to purify telomerase involves separating the telomerase from other organic biomolecules according to molecular size, shape, or buoyant density and collecting the telomerase. This can be the fifth step in the six-step purification procedure outlined in FIG. 3. A preferred embodiment of this step involves fractionating the telomerase preparation by gel filtration chromatography. Sizing gel matrices that separate proteins in the size range of 200 kDa to 2000 kDa are most useful in human telomerase purification. Preferred matrices are HW65 (TosoHaas, Montgomeryville, Pa.) and, in particular, Superose® 6 (Pharmacia, Uppsala, Sweden). Another embodiment of this step involves gradient centrifugation of the telomerase in gradients of different compositions that yield separation of the molecules in the preparation. Preferred gradients are composed of $Cs_2SO_4$ or of glycerol. Another embodiment of this step involves the use of gel electrophoresis, which separates molecules based on their charge, size and shape. The gel compositions may vary widely in this embodiment. A preferred gel is a native gel, composed of agarose, polyacrylamide, or both, that is run under physiological conditions of buffer strength and pH, which tend to preserve the native complex and activity of human telomerase.

After the high capacity purification steps, and optionally after the intermediate purification steps, telomerase is further purified by contacting the telomerase with an affinity agent having specific affinity for telomerase, separating telomerase from other organic biomolecules that do not bind to the affinity agent, and collecting telomerase from the affinity agent. Affinity agents in this step of the purification method are orders of magnitude more specific for binding telomerase over other organic biomolecules, than are the agents in the other steps of the method. Affinity agents having specific affinity for telomerase include, for example, oligonucleotides that are complementary to the RNA component of telomerase, oligonucleotides (RNA or DNA) having a primer sequence recognized by telomerase, antibodies that recognize epitopes of telomerase, and compounds that inhibit telomerase. The preferred affinity agent is Oligo 5, an oligonucleotide whose sequence is given in Table 2. "Peptide nucleic acids," polymers having an amide backbone and attached bases, are also useful as affinity agents.

In one embodiment of this step, an oligonucleotide complementary to a sequence of the RNA component of telomerase is attached to a retrievable label, e.g., biotin. The label can be on one or both ends. After contacting the telomerase with the labeled affinity agent, the affinity agent is contacted with a binding agent that binds to the retrievable label, e.g., streptavidin or derivative agent. Preferably, the binding agent is attached to a matrix. Then, molecules that have not bound to the retrievable affinity agent, and therefore are not bound to the binding agent, are separated or removed from the mixture. By releasing telomerase from the affinity agent, telomerase is purified.

The use of retrievable labels is well known in the art. The retrievable label and binding agent can be any sort of ligand and ligand partner. In a preferred embodiment, the retrievable label is biotin and the binding agent is ImmunoPure® NeutrAvidin (Pierce, Rockford, Ill., catalog number 53157). In one embodiment, the retrievable label is an antigen and the binding agent is an antibody that binds the antigen.

A general experimental procedure for testing nucleic acid affinity approaches is as follows: (i) biotin-labeled oligonucleotides are mixed under various conditions with partially purified telomerase; (ii) beads with attached NeutrAvidin are added to the mixture; (iii) beads are separated from the mixture (telomerase that has stuck to the oligonucleotide has also stuck to the beads, so activity is depleted from the mixture); (iv) beads are washed to remove bound material (telomerase comes off the beads, and activity is recovered).

Oligonucloetides complementary to a sequence of the RNA component of human telomerase were tested for their ability as affinity agents. Oligonucleotides useful in the methods of the invention are given in Table 1. Each of the antisense oligos was tested in parallel with a control non-specific oligo. Depletion refers to the retention of telomerase by the oligo; recovery refers to the subsequent release of telomerase from the oligo. Of the antisense sequences tested, Oligo 5 is the preferred oligonucleotide for an affinity purification. While not wishing to be bound by theory, Oligo 5 is a strong non-processive primer, so it may not be acting as an antisense ligand; it may be acting as a primer ligand.

Using Oligo 5 and eluting with varying salt concentrations, telomerase activity has been recovered in a set of fractions containing low levels of detectable protein (10 μg/mL), making this a highly enriched preparation of telomerase. The yield of telomerase activity was 29%. (See Example III).

TABLE 1

Oligonucleotides complementary (antisense) to human telomerase RNA.

| Oligo Name | Size (nt) | Description | Performance |
| --- | --- | --- | --- |
| anti-P | 31 | Direct antisense hTR, covers template | Good depletion, inhibits activity. |
| P3 | 22 | Antisense hTR plus a primer terminus | Good depletion, recovery of telomerase. |
| Oligo 5 | 30 | Antisense hTR | Good depletion, recovery of telomerase. |
| Oligo 13 | 30 | Antisense hTR | Some depletion. |
| Oligo 14 | 30 | Antisense hTR | Good depletion. |

TABLE 2

| | Oligonucleotide Sequences |
| --- | --- |
| anti-P | [SEQ ID NO:1]<br>5' BIOTIN - GCC TAC GCC CTT CTC AGT TAG GGT TAG ACA - A - 3'BIOTIN |
| P3 | [SEQ ID NO:2]<br>5' - BIOTIN CGC CCT TCT CAG TTA GGG TTA G - 3' |
| Oligo 5 | [SEQ ID NO:3]:<br>5' - BIOTIN GCC GAG TCC TGG GTG CAC GTC CCA TAG CTC - 3' |
| Oligo 13 | [SEQ ID NO:4]:<br>5' - BIOTIN GAA CGG GCC AGC AGC TGA CAT TTT TTG TTT - 3' |
| Oligo 14 | [SEQ ID NO:5]:<br>5' - BIOTIN GCT CTA GAA TGA ACG GTG GAA GGC GGC AGG - 3' |

In another embodiment of this step, the affinity agent is an oligonucleotide having a primer sequence recognized by telomerase. The oligonucleotide is contacted with the telomerase and dideoxy nucleotides under conditions for a primer elongation reaction. This results in chain termination of DNA synthesis by telomerase. Under these conditions, telomerase may lock on the chain terminated primer. The primer and the telomerase attached to it is isolated. The oligonucleotide preferably includes sequences that have been found to be efficient telomeric primers in the primer elongation assay. This includes the sequence synthesized by telomerase as well as non-telomeric sequence primers such as M2/TS. For example, human telomerase synthesizes telomeric DNA sequences [TTAGGG]$_n$ onto the 3' end of single-stranded DNA (and RNA) primers. Thus, an oligonucleotide for isolating human telomerase can have the sequence [TTAGGG]$_3$ [SEQ ID NO:6] Sequences synthesized by other telomerase are identified in, for example, E. H. Blackburn, (1991) TIBS 16:378–381.

The above embodiment was tested using biotinylated oligonucleotides as primers, which were subsequently retrieved with NuetrAvidin beads.

Controls were non-primer oligos, such as [CCCTAA]$_3$ [SEQ ID NO:7]. Preferred oligonucleotides for affinity purification in this embodiment are M2/TS and [TTAGGG]$_3$ [SEQ ID NO:8]. The sequence of useful oligonucleotides is given in Table 3.

TABLE 3

| Oligo Name | Size (nt) | Description | Performance |
| --- | --- | --- | --- |
| [TTAGGG]$_3$ [SEQ ID NO: 6] | 18 | Telomeric primer | Good depletion, recovery of telomerase |
| M2/TS | 18 | Non-telomeric primer | Good depletion, recovery of telomerase |
| Photo-SS-[TTAGGG]$_3$ [SEQ ID NO: 6] | 18 | Cleavable telomeric primer | Slight depletion, some recovery |

Oligonucleotide Sequences:

```
M2/TS
5'-BIOTIN-AAT CCG TCG AGC AGA GTT-3' [SEQ ID NO:8]
```

With the various primer oligos used, the efficiency of depletion correlated with the strength of the primer in a telomerase primer elongation assay. The M2/TS primer showed the best ability to deplete and retain the activity. Some telomerase activity was eluted with DTT from a biotinyl-SS-[TTAGGG]$_3$ [SEQ ID NO:6] primer depletion (the DTT breaks the disulfide linkage in the primer, releasing it from the beads). The yield was only 1–5%, but the purity was likely high (protein concentration was below detection by standard protein assay).

In another embodiment of this step, the affinity agent is an antibody (or binding fragment of it, e.g., Fab fragments) that recognizes an epitope of telomerase. One source of antibodies that may recognize human telomerase are antibodies that recognize the telomerase of other organisms. Those antibodies may cross react with human telomerase due to homology. Primary sequences of the 80 kDa and 95 kDa protein subunits of Tetrahymena telomerase have been analyzed for regions of antigenicity and surface probability. From this analysis, two peptides for the 80 kDa and one for the 95 kDa have been designed. These peptides have the following sequences:

```
GP 80A:
CRKKTMFRYLS VTNXQKWDQT KKKRKEN      [SEQ ID NO:9]
-80 kDa protein

GP 80B:
CHISEPKERV YKILGKKYPK TEEE          [SEQ ID NO:10]
-80 kDa protein

GP 95A:
DNNLCILALL RFLLSLERFN IL            [SEQ ID NO:11]
-95 kDa protein
```

These peptides were used to raise antibodies. In choosing Tetrahymena protein sequences for this purpose, selecting for surface probability is very important because antibodies against external features of telomerase are most likely to immunopreciptate the telomerase activity from other organisms. In another embodiment, antibodies are raised against fusion proteins bearing a portion of a telomerase polypeptide component and made in, e.g., an E. coli expression system. In another embodiment, the antibodies are from humans afflicted with autoimmune disease. In another embodiment, antibodies are identified from among antibodies that recognize epitopes on enzymes that are functionally related to telomerase, e.g. DNA replication enzymes and reverse transcriptases. In another embodiment, the antibodies are raised against peptides from the sequence of human telomerase proteins.

In another embodiment of this step, the affinity agent is an inhibitor of telomerase activity that binds to telomerase. Telomerase inhibitors and methods of assaying for them are described in U.S. patent application Ser. No. 08/288,501, filed Aug. 10, 1994, incorporated herein by reference. When attached to a retrievable label, these compounds provide a hook by which to isolated telomerase.

After the molecules that do not bind to the affinity agent are removed, the bound telomerase is released from it. When the affinity agent is an oligonucleotide, extremes of ionic strength (e.g., high (about 500 mM NaCl) or low (zero) salt), exposure to high concentrations of nucleotides, and the use of cleavable oligos (disulfide oligos shown in Table 3) have been tried in efforts to release the bound enzyme. Washing an Oligo 5 column with salt solutions of increasing ionic strength releases telomerase.

When the M2/TS affinity column matrix with bound telomerase was boiled, and the released material was analyzed on a silver stained SDS gel, there were very few bands apparent (less than 10). While in this experiment telomerase proteins were likely below the limit of detection, this result indicated that very few other proteins were bound to the affinity matrix. Thus the specificity of this affinity depletion was high.

EXAMPLE I

Telomerase Assay Protocols

A. Primer Elongation Assay
a) Assay

The primer elongation assay described in this example is the standard for determining specific activity for the purposes of determining relative purity of a telomerase preparation.

The 40 μl telomerase reaction should have a final concentration of:
1. 1X Telomerase Buffer (see below)
2. 1 mM $MgCl_2$
3. 2 mM DATP, 2 mM dTTP, 8 μM dGTP
4. 1 μM or 0.25 μg/reaction of oligo primer M2/TS
5. 20 μCi/reaction of ($\alpha^{32}$P-dGTP (0.624 μM dGTP, spec. activity 800 Ci/mmol; NEN)

1. To start the reaction, combine 20 μl of the 2× reaction mix with an equal volume (20 μl) of enzyme extract.
   For RNase control, add 1 μl of RNase A at 5 mg/mL to buffer mix just before adding extract.
   (Final concentration of RNase is 125 μg/mL)
2. Incubate at 30° C. for 90 min (total volume=40 μl).
3. To stop reaction, add 50 μl of TE stop solution (10 mM Tris pH 7.5 and 20 mM EDTA) containing 100 μg/mL of RNase A (Stock=10 mg/mL; 100× dilution). Final concentration is 55 μg/mL}.
4. Incubate at 37° C. for 15 min (total volume=90 μl).
5. To eliminate proteins add 50 μl of 10 mM Tris pH 7.5, 0.5% SDS, and 300 μg/mL proteinase K. (Final concentration of PK is 107 μg/mL, and 0.18% SDS; make up fresh each time).
   For 1 mL: 10 μl 1.0 M Tris
   25 μl 20% SDS
   30 μl PK (10 mg/mL)
   0.935 mL Depc water 6. Incubate at 37° C. for 15 min (total volume=140 μl).
7. Extract with an equal volume (140 μl) of PCIA (phenol:chloroform:isoamyl alcohol (25:24:1)). Transfer aqueous phase to fresh tube.
8. Precipitate DNA by adding 40 μl of 2.5 M $NH_4OAC$ (good for precipitating small oligos) containing 100 μg/mL of tRNA (10 mg/mL stock; 100× dilution. 30 μg carrier/tube) and 2–3 volumes (500 μl) of cold absolute ethanol.
9. Let sit −20° C. for 30 min or overnight.
10. Spin in microcentrifuge for 15 min at room temperature.
11. Discard supernatant and dry pellet in a speed-vac, or air dry overnight.
    Optional; rinse pellet with 50 μl of cold ethanol.
12. Resuspend pellet in 3 μl of sequencing loading dye (99.9% formamide, 0.05% xylene cyanol, and 0.05% bromphenol blue).
13. Boil for one minute, and chill on ice.
14. Load samples onto an 8% acrylamide/7 M urea sequencing gel and run at 1500 V (50 W). (until BPB is about ⅔ to ¾ of the way down).
15. Transfer gel onto Whatman filter paper and dry at 80° C. for 35 minutes, and cool for 15 min before removing gel from dryer.
16. Expose gel to phosphoimager screen (Molecular Dynamics). Typical exposures are between 6 and 24 hours.

b) Human Telomerase Assay Solutions 1. 10X Telomerase Buffer

| Component amt/10 mL | (stock) | (10x) | (1x) | for 10 mL of 10x |
|---|---|---|---|---|
| 1. Tris.Cl pH 7.5 | 1 M | 500 mM | 50 mM | 5 mL |
| 2. Spermidine.3HCl | 1 M | 10 mM | 1 mM | 100 μl |
| 3. BME* | 14.3 M | 50 mM | 5 mM | 35 μl |
| 4. $MgCl_2$ | 1 M | 10 mM | 1 mM | 100 μl |
| 5. K-OAc | 5 M | 500 mM | 50 mM | 1 mL |
| 6. EGTA | 0.5 M | 10 mM | 1 mM | 200 μl |
| | | | | DEPC 3.565 mL |

*Alternatively, make (−)BME, aliquot 1 mL. Add 3.5 μl BME to give 10x before use.

2. Stop Solution

| Component | (stock) | (final) | amt/10 mL |
|---|---|---|---|
| 1. Tris.Cl pH 7.5 | 1 M | 10 mM | 100 μl |
| 2. EDTA | 200 mM | 20 mM | 1 mL |

3. Cold dNTP's
   Use e.g., Pharmacia (Uppsala, Sweden), 100 mM stocks.
   Combine 10 μl of dATP and 10 μl of dTTP in one tube and store at −20° C. or −70° C.
   Do not use the same tube more than 3× since dNTP's are unstable with repeated freeze/thaws. If making a dilution, use 10 mM Tris.Cl pH 7.5 (do not use water since the acidic pH will destroy the nucleotide).

4. Oligo Primer
   Prepare sequence on synthesizer or buy commercially (e.g., Operon).
   Gel (10% acrylamide/7M Urea) purify the crude oligo, and concentrate using a C-18 column. Dry in a speed-vac, and resuspend pellet in 10 mM Tris.Cl pH 7.5. A 30% to 45% yield is usually obtained. About half of the oligo is lost during gel purification, and 5% to 30% is lost from the column. Preferably purify 300 to 600 µg and resuspend final pellet in 40 µl of buffer. Determine the concentration by reading the absorbance at 280 nm. Assume for an oligo that 1 OD=30 µg/mL.

B. Telomerase Activity Dot Blot Assay
1. Combine components of Assay Mix:

|  | Vol | Stock | Final Conc (in 40 µl) |
|---|---|---|---|
|  | 4.0 µl | 10X HTB | 1X |
|  | 0.4 µl | 100 mM dATP | 1 mM |
|  | 0.4 µl | 100 mM dGTP | 1 mM |
|  | 0.4 µl | 100 mM dTTP | 1 mM |
|  | 1.0 µl | 0.25 µg/mL Oligo M2/TS | 1 µM |
|  | 13.9 µl | depc $H_2O$ |  |
| $V_t=$ | 20.0 µl |  |  |

2. Add 20 µl of test extract, mix and incubate at 30° C. for 90 min.
3. Add 160 µl of 0.5 M NaOH, 12.5 mM EDTA (Final Conc=0.4 M, 10 mM), mix, and let sit at room temp for 5 min.
4. Transfer samples to a Silent Monitor, Biodyne® B (0.45 µM) 96-well plate, then place plate on vacuum manifold to filter sample.
5. Turn off vacuum and add 200 µl 0.4 M NaOH to wells, and apply vacuum until filter is quite dry.
6. Peel off membrane filter, rinse in 2×SSC (to neutralize NaOH), and place in 50 mL of prewarmed prehybridization mix (6×SSC, 1× Denhardt's, 20 mM NaPhos pH 7.2, 0.4% SDS, depc $H_2O$) for 1 hour at 65° C.
7. Make riboprobe using Stratagene RNA transcription kit (HindIII-digested pBLRep4 DNA template, T3 RNA polymerase). To stop the reaction, add 1 µl of RNase-free DNase and incubate at 37° C. for 15 min, PCIA extract (equal vol), add 1/10 vol of 3 M NaOAc and 2.5 vol of ethanol to precipitate the RNA probe. Centrifuge 10 minutes and dissolve RNA in 100 µl TE in depc (diethylpyrocarbonate) $H_2O$.
8. Hybridize blot by adding 50 µl of probe per filter and incubate overnight at 65° C.
9. Next day, heat wash solution (1×SSC, 0.1% SDS) to 65° C. and transfer filter to wash solution. Rinse quickly, transfer filter to fresh solution, discard wash into radioactive waste and repeat. Wash four more times for 15 minutes each at 65° C.
10. Remove filter from wash solution and drain off excess liquid. Seal in bag and expose to PI screen for 1 hour. Scan screen and quantitate using grid.

C. RT-PCR Assay
a. RNA Preparation:
1. RNA is extracted from column fraction: 300 µl/reaction.
2. Prepare 1 mL 10% SDS, 100 mM EDTA solution freshly before use: 200 µl stock 500 mM EDTA, 800 µl stock 10% SDS up to 1 mL.
3. In each reaction, add 30 µl of above SDS, EDTA buffer and 5 µl of stock Proteinase K (10 µg/µl) to each reaction, so the final concentration is: 1% SDS, 10 mM EDTA, 50 µg proteinase K.
4. Incubate at 37° C. for 10 min.
5. Phenol:Chloroform extract twice (be careful not to take the white interphase material).
6. To the final supernatant, 30 µl of 3 M sodium acetate is added, and the nucleic acids are precipitated by addition of 900 µl 100% ethanol and incubation at −70° C. or dry ice for 30 min.
7. To spin down the precipitate, microcentrifuge at full speed for 15 minutes, draw out all liquid, and use 200 µl 85% ethanol to rinse the pellet, then use speedy-vac to dry the pellet.
8. Resuspend the pellet in 30 µl Depc water. Take 1 µl resuspension into 100 µl Depc water, and read $OD_{260\ nm}$. Use OD260=40 µg/mL to calculate RNA concentration.

b. First Strand cDNA Synthesis.
1. Take 0.1 to 1 µg RNA made form each telomerase fractions, and is mixed with 40 to 80 ng random hexamer, up to 10 µl.
Random hexamer, from e.g., Pharmacia $pd(N)_6$, total 50 OD unit powder/vial. Use 90 OD unit/mL=2.97 mg/mL, which is 1 OD unit=33 µg.
2. Denature at 95° C. for 10 min, chilled on ice, and spin down the vapor on the top of Eppendorf tube.
3. Prepare the reaction mixture:

|  | 1 Rx | 13 Rx |
|---|---|---|
| 5x 1st stand sys. buffer (BRL): | 4 µl | 52 µl |
| 0.1 M DTT (BRL): | 2 µl | 26 µl |
| 10 mM dNTP (BRL): | 1 µl | 13 µl |
| RNAguard ® (Pharmacia): | 1 µl | 13 µl |
| Depc $H_2O$: | 1 µl | 13 µl |
| TOTAL: | 9 µl | 117 µl |

Add 9 µl/each reaction, and incubation at 42° C. water bath.
4. After 1–2 min incubation, 1 µl Superscript II RTase (BRL) is added to the mixture, and incubated for 60 min at 42° C.
5. Stop the reaction by heating the tube for 10 min at 95–98° C. Chill on ice, and spin down the vapor.

c. PCR Amplification of cDNA with Specific Primer Set
1. PCR reaction buffer:

|  | 1 Rx | 13 Rx |
|---|---|---|
| primer 1: | 1 µl | 13 µl |
| primer 2: | 1 µl | 13 µl |
| 2.5 mM dNTP: | 2.5 µl | 32.5 µl |
| 5 µ/µl Taq polymerase (BM): | 0.4 µl | 5.2 µl |
| 5 mg/mL T4 gene 32 protein (BM): | 0.04 µl | 0.52 µl |
| 10 × TCR buffer (BM): | 2 µl | 26 µl |
| 10 µCi/µl α-32P dATP | 0.5 µl | 6.5 µl |
| Depc $H_2O$: | 10.56 µl | 137.28 µl |
| TOTAL: | 18 µl | 234 µl |

In 2 µl of first strand cDNA, add 18 µl of above PCR reaction buffer. One drop of mineral oil is then added to each PCR tube.
2. Set up condition of PCR amplification for hTR clone: 94° C. for 34 sec, 72° C. for 45 sec, 72° C. for 1.5 min, 20 cycles.
3. After PCR, 5 µl of the product is mixed with 10×DNA sequencing loading dye, and loaded on 6% native polyacrylamide gel (do not need to pre-run the gel). Run at 250 volts for 90 min. Dry the gel and PI exposure.

It will be clear that one can substitute known equivalents in the above protocols.

D. Telomerase RNA Detection by Northern Analysis

1. Gel Parameters 20 cm long gel 1 mm comb with 16 wells

5% Acrylamide gel/7 M Urea in 1×TBE

Run the gel O/N at 125 V for about 12 hr. (the BPB and XC will have run off the gel). U2 will be near the bottom, and hTR will be about ¼ of the way down into the gel.

hTR runs at about 700 nt with respect to DNA markers when using a 5% gel. It appears as a doublet.

RNA pellets (made from 50 to 100 µl of a telomerase fraction) are resuspended in 15 µl of sequencing dye (deionized formamide with dye), boiled for a few minutes and quick chilled before loading.

Note:

If a 1 mm thick 6% gel is used, and run overnight, hTR runs at about 1 kb.

If a 0.4 cm thick 5% gel is used, and run at 1000 V (35–40 W), hTR runs at about 450 nt. hTR runs as a single band using this method, but if the fractions are not purified, the samples smear and the signal will be poor.

2. EtBr Staining

Stain the gel for 20–30 min in 0.5 µg/mL of EtBr in 1×TBE to see the snRNP profile.

3. Electroblotting

Genie Transfer apparatus.

The transfer is done onto Hybond N+.

Transfer; rT° in 1×TBE for 0.7 hr, using 0.95 A.

4. Fixing RNA onto Membrane

UV-crosslink using a Stratagene crosslinker; autosetting (120 mJ).

Crosslink with the RNA on the membrane face up.

5. Probe

Use either PCR (R3C and U3B primers) to make a radioactive 154 nt fragment, or I hexamer label the 154 nt hTR fragment using Klenow. Probe at 65° C., and the final wash is in 0.1×SSC. Perform blot using Church Protocol (below).

6. Phosphor-Imager Analysis

Expose the blot for 5 hr on a phosphor-imaging plate (e.g., Fuji). The exposure time can be shortened when using concentrated extracts. Film exposure: 2–7 days, depending on the signal.

E. Church Protocol

Prehybridize in 50 to 100 mL of Church solution (500 mM $Na_2HPO_4$ pH 7.2, 1 mM EDTA, 1% BSA, and 7% SDS). Prehybridize a few hours at 65° C.

Probe with 0.1 µg of $^{32}$P-5' end labeled oligo (forward reaction) (specific activity of probe should be ~$10^8$–$10^9$ cpm/µg). Probe overnight at 65° C.

Remove blot from bag at room temperature and rinse manually in 2×SSC (heated to hybridization T°) twice, for 1 min per wash, 500 mL per wash. This is to quickly get rid of hot label which might non-specifically stick to the membrane.

Wash blot 5×, in 2×SSC (rT°), 0.1% SDS, 5 minutes per wash, 500 mL per wash at rT°.

Wash blot 1×, in 0.1×–2×SSC and 0.1% SDS at hybridizing temp. (500 mL) for 30 min.

Place wet blot on filter paper, wrap with Saran or bag, and expose to film O/N.

Notes:

1. If doing more than one blot, start rinsing the second blot after the first blot is in the second 5 minute wash.

2. Washes for 1 blot: 4 liter; 400 mL 20×SSC and 3600 mL dd$H_2O$. Remove 1 liter and add 15 mL 20% SDS to 3 liter. (2×SSC=300 mM NaCl, therefore about half that of hybridizing salt concentration).

3. Church solution (100 mL): 1 g BSA to 50 mL 1 M $NaPO_4$ pH 7.2, 15 mL $H_2O$, dissolve, then add 0.2 mL 0.5 M EDTA, and 35 mL 20% SDS.

EXAMPLE II

Protocols for Crude Cell Extract from 293 Cells

This preparation prefers a minimum of $10^7$ cells, either suspension or adherent cells. It can be scaled up for larger numbers of cells proportionally. Preparation of as much as $7.7×10^{10}$ cells has been done with excellent activity but slightly higher background. Furthermore, the whole procedure should be performed at 4° C. and on ice.

Grow cells to midlog phase. Adequate additional cells for counting should be provided: the calculation of buffer amounts is dependent on the number of cells rather than volume.

Either CHAPS or CHAPSO detergent can be used. These show little differences in obtaining active extracts.

A. Buffers

Wash Buffer

| Stock | Final | 20 mL | 100 mL |
|---|---|---|---|
| 1 M HEPES pH 7.5 | 10 mM | 200λ | 1 mL |
| 1 M $MgCl_2$ | 1.5 mM | 30λ | 150λ |
| 1 M KCl | 10 mM | 200λ | 1 mL |
| 1 M DTT | 1 mM | 20λ | 100λ |
| DEPC $H_2O$ | | 19.55 mL | 97.75 mL |

Lysis Buffer (0.5% CHAPS/CHAPSO)

| Stock | Final | 10 mL | 50 mL | 60 mL |
|---|---|---|---|---|
| 1 M Tris Cl pH 7.5 | 10 mM | 100λ | 500 µl | 600 µl |
| 1 M $MgCl_2$ | 1 mM | 10λ | 50 µl | 60 µl |
| 0.5 M EGTA | 1 mM | 20λ | 100 µl | 120 µl |
| 0.1 M PMSF | 0.1 mM | 10λ | 50 µl | 60 µl |
| BME | 5 mM | 3λ | 15 | 18 µl |
| 10% Detergent | 0.5% | 500λ | 2500 µl | 3000 µl |
| 100% Glycerol | 10% | 1 mL | 5 mL | 6000 µl |
| DEPC $H_2O$ | | 8.36 mL | 41.785 mL | 50.14 mL |

B. Procedure

1. For adherent cells, grow two sets of 15 cm plates and use one for counting. Once cell count has been determined, rinse the other set twice with 20 mL of cold PBS. Add 10 mL PBS and scrape the cells into a 15 mL centrifuge tube. Continue to step 3.

2. For suspension cultures, grow to a density not exceeding $10^6$ cells/mL (about 6–7×$10^5$/mL is preferred). After establishing cell count, pellet cells in 50 mL centrifuge tubes at 200 g/4° C./5 min. Resuspend in cold PBS equivalent to original volume.

3. Pellet the cells in a clinical centrifuge at 200 g/4° C./5 min. Resuspend thoroughly in Wash Buffer at a concentration of $10^6$ cells/100 λ and transfer to microcentrifuge tubes. Spin cells down at 13 k rpm for 1 minute.

4. Remove Wash Buffer and resuspend pellet in detergent lysis buffer at a concentration of $10^6$ cells/18.5 λ and transfer to appropriate ultrafuge tube (see below). Leave on ice for 30 min. Parafilm top of tube if deemed necessary.

| Volume | Beckmann Centrifuge Tube | Rotor |
|---|---|---|
| <1 mL | thick-walled micro polyallomer | TLS 55 |
| 1.2 mL | thin-walled micro polyallomer | TLS 55 |
| 2–5 mL | polyallomer | SW 41 |

5. Prepare the proper swinging bucket ultrafuge rotors and chill the appropriate ultracentrifuge to 4° C. For the SW41 rotor, set the XL-80 Ultra at 28.5 k rpm for 100,000 g. For the TLS 55 rotor, set the tabletop Ultra at 39 k rpm.

6. Spin the lysed cells for 30 minutes.

7. Collect the clear aqueous portion of the supernatant (this is the extract). Aliquot the extract into 100 λ portions and freeze on dry ice. Store at −80° C.

EXAMPLE III

Four Step Method for Purifying Telomerase

A method of making human telomerase that is 3,550-fold purified compared to that in crude cell extracts is described. This method comprises four steps in succession:

1) CHAPS detergent S-100 extract preparation from 293 cells;
2) chromatography of the S-100 extract on POROS® 500 HQ matrix;
3) chromatography of the POROS® 50 HQ active fractions on POROS® 20 Heparin HE-1 matrix; and 4) chromatography of the POROS® 20 Heparin HE-1 active fractions on Oligo 5 affinity matrix. Protocols for each step are provided.

In the first step, $7.3\times10^{10}$ 293 cells were collected from 128 liters of suspension culture and CHAPS extracted as described in Example II to yield 883 mL of CHAPS S-100 extract.

In the second step, this extract was subjected to chromatography on a POROS® 50 HQ column, and fractions containing telomerase activity were combined for a total active pool of 72 mL. This step was performed as follows:

POROS® 50 HQ resin [PerSeptive Biosystems, Cambridge, Mass., catalog number 1-2559-05] was resuspended in an equal volume of buffer A [20 mM Hepes pH 7.9, 2 mM $MgCl_2$, 1 mM EGTA, 10% glycerol, 0.1% Nonidet P-40, 1 mM Dithiothreitol, 0.2 mM Phenylmethylsulfonylfluoride, 1 mM Benzamidine, 1 mM Sodium Metabisulfite] equilibrated with 100 mM NaCl [buffer A/100 mM NaCl] and the slurry was packed by gravity in a XK 26/20 chromatography column [Pharmacia, Uppsala, Sweden, catalog number 18-1000-72].

The column was run on a GradiFrac® system [Pharmacia, Uppsala, Sweden, catalog number 13-2192-01]. The column was equilibrated with 3 column volumes of buffer A/100 mM NaCl, followed by a high salt wash with 3 column volumes of buffer A/2000 mM NaCl. Finally, the column was re-equilibrated with 3 column volumes of buffer A/100 mM NaCl. Binding capacity of the column was determined by loading increasing amounts of CHAPS extract until telomerase activity was detected in the flow through fractions. Capacity of POROS® 50 HQ was found to be in the range of 20 milligrams of CHAPS extract per milliliter of resin.

1.6 grams of CHAPS extract was loaded on a 80 mL POROS® 50 HQ column at a flow rate of 20 mL/min. The column was then washed with 3 volumes of buffer A/100 mM NaCl. A first elution was performed by washing the column with a 3 column volume medium salt step [buffer A/480 mM NaCl]. Telomerase activity was recovered by a high salt step [buffer A/1050 mM NaCl]. Fractions from the high salt elution were dialyzed separately against buffer A overnight. Fractions were scanned for telomerase activity by primer elongation assay. Active fractions were pooled. This was repeated several times to process the entire 6.8 grams of CHAPS S-100 extract.

Figure 4:
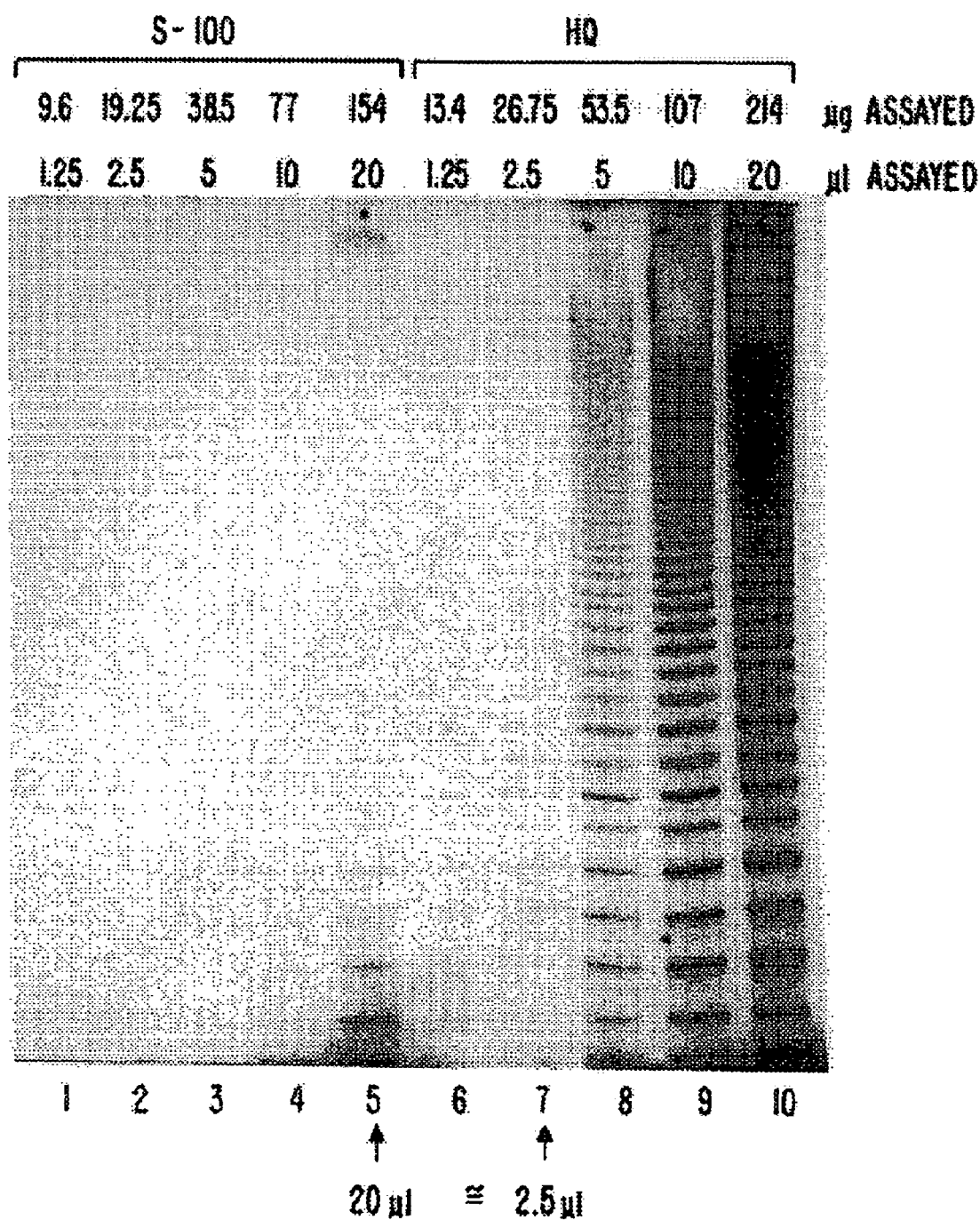
FIG. 4 shows the results of a primer elongation assay from a CHAPS S-100 extract of 293 cells (lanes 1–5) and from the POROS® 50 HQ anion exchange chromatography active pool (lanes 6–10) in the four-step purification procedure.

To determine the relative specific activity of telomerase for the CHAPS S-100 extract and the POROS® 50 HQ active pool, protein concentrations for each were determined (Coomassie Protein Assay Reagent, Pierce Product #23200, Rockford, Ill.), and the preparations were compared for relative telomerase activity by the primer elongation assay described in Example I. (FIG. 4.) The dried gel was exposed to a phosphorimaging screen for 4–16 hr. The screen was scanned and the gray scale adjusted in order to produce an image that appeared linear with respect to the corresponding assay titration. That was usually between 5–25 at the lower end and 1000–2000 at the upper end.

Telomerase activity was measured in arbitrary units and was derived from a visual assessment of the signal resulting from a titration of fractions over a 10–20 fold range in 2-fold increments. Relative comparisons of activity between fractions were determined from the linear range of each titration.

Lanes 1 to 5 of FIG. 4 show primer elongation products from telomerase activity in 1.25 µl to 20 µl of the CHAPS S-100 extract; lanes 6 to 10 show the same from a titration of the POROS® 50 HQ active pool. The quantity of telomerase products increases in proportion to the quantity of preparation assayed in lanes 3 to 5 and in lanes 6 to 10, providing a linear range for comparison between the two preparations. From the linear range for each preparation, it was estimated that 20 µl of the CHAPS S-100 extract. (lane 5) generates the same quantity of telomerase primer elongation products as 2.5 µl of the POROS® 50 HQ active pool (lane 7). Hence, these volumes each contain one arbitrary unit of telomerase activity. This arbitrary unit is only relevant for this particular comparison.

Using the measurements of volume, protein concentration, and volume per telomerase activity unit, simple calculations provide the total units and total protein amount, from which the relative specific activity of telomerase was derived for the two preparations (Table 4). The specific activity of the POROS® 50 HQ active pool (0.037 units/µg) is 5.8 times greater than that of the CHAPS S-100 extract (0.0065 units/µg). Therefore, the human telomerase in the POROS® 50 HQ active pool has 5.8-fold increased relative purity compared to that in the CHAPS S-100 extract. The total units of telomerase activity in the POROS® HQ active pool (28,800 units) represents 65% of that in the CHAPS S-100 extract (44,150 units). Therefore, the POROS® HQ chromatography has a yield of 65% for telomerase activity.

In the third step, 24 mL of a POROS® 50 HQ active pool was subjected to chromatography on a POROS® Heparin 20

HE-1 column, and fractions containing telomerase activity were combined for a total active pool of 6 mL. Chromatography was carried out as follows.

POROS® 20 HE-1, was obtained from PerSeptive [Cambridge, Mass., catalog number 1-5229-06]. Handling of the resin, packing and equilibration of the column was performed in the exact same way as described for the previous resin, except that a XK 16/20 chromatography column [Pharmacia, Uppsala, Sweden, catalog number 18-8773-01] was used. Binding capacity was determined to be in the range of 15 mg/mL resin.

146.4 milligrams of POROS® 50 HQ pooled material were loaded on a 25 mL POROS® Heparin HE-1 column at a flow rate of 15 mL/min. The column was then washed with 3 volumes of buffer A/100 mM NaCl. A first elution was performed by washing the column with a 3 column volume medium salt step [buffer A/347 mM NaCl]. Telomerase activity was recovered by a high salt step [buffer A/1430 mM NaCl]. Fractions from the high salt elution were dialyzed separately against buffer A overnight. Fractions were scanned for telomerase activity by primer elongation assay. Active fractions were pooled.

Figure 5:
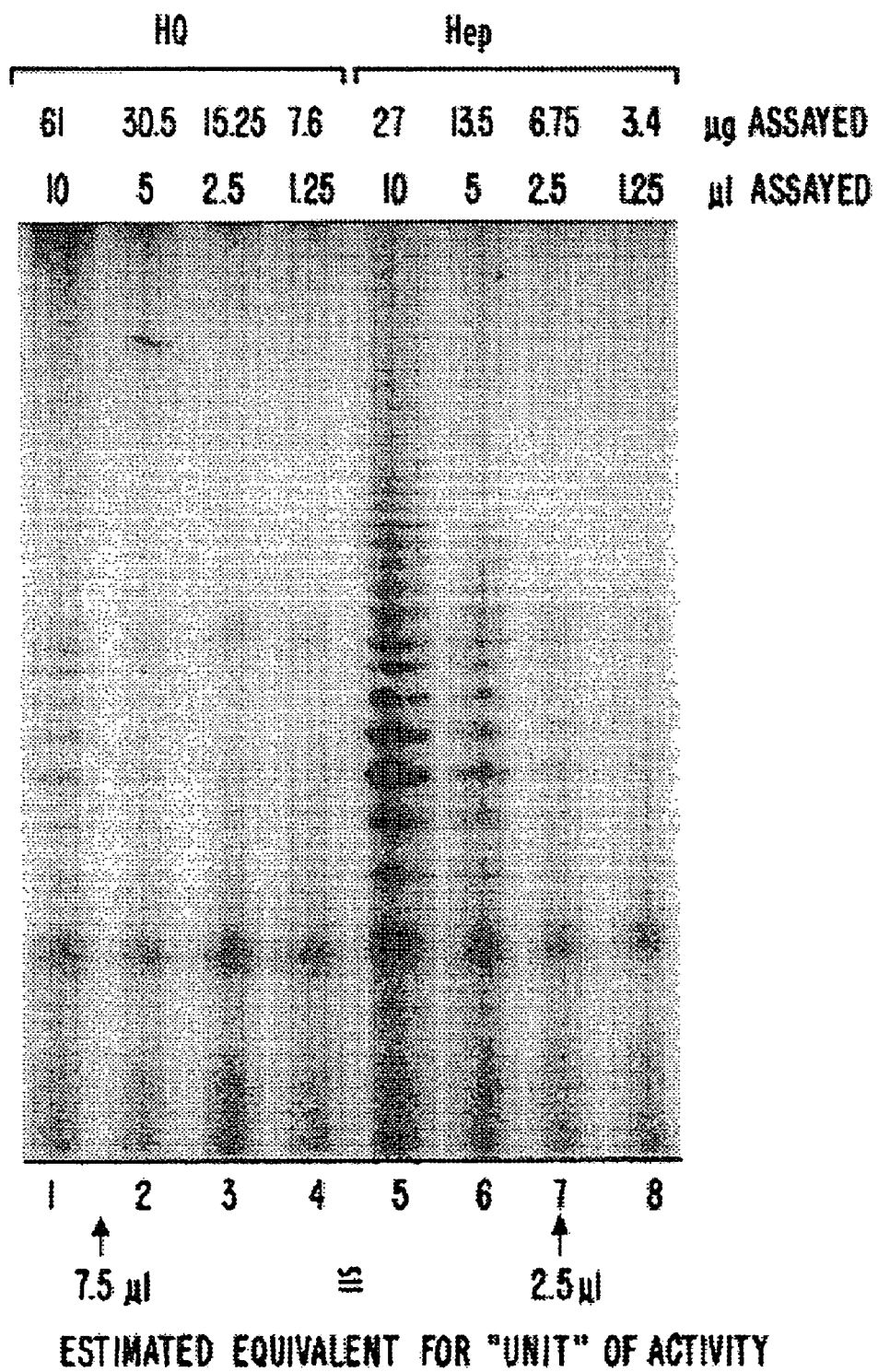
FIG. 5 shows the results of a primer elongation assay from a telomerase preparation from the POROS® 50 HQ anion exchange chromatography active pool (lanes 1–4) and the POROS® Heparin 20 HE-1 chromatography active pool (lanes 5–8) in the four-step purification procedure.

The relative specific activity of telomerase for the POROS® 50 HQ active pool and the POROS® Heparin 20 HE-1 active pool was determined exactly as described above for the previous step. Titrations of the two preparations in the primer elongation assay are shown in FIG. 5; measured and calculated values are shown in Table 4. These data indicate that the human telomerase in the POROS® Heparin 20 HE-1 active pool is 6.8-fold purified compared to that in the POROS® 50 HQ active pool. The cumulative purification after this third step is the product of all previous steps. Hence, the human telomerase in the POROS® Heparin 20 HE-1 active pool has 6.8×5.8=39.4-fold increased relative purity compared to that in the CHAPS S-100 extract. The yield of the POROS® Heparin 20 HE-1 chromatography is 75% for telomerase activity, and the cumulative yield after this third step is 49%.

In the fourth step, 0.14 mL of a POROS® Heparin 20 HE-1 active pool was subjected to chromatography on an affinity matrix using Oligo 5 as the affinity ligand. Fractions from the affinity column that contained telomerase activity were combined for a total active pool of 0.4 mL. Affinity chromatography was performed as follows.

UltraLink™ Immobilized NeutrAvidin beads [Pierce, Rockford, Ill., catalog number 53151] were pre-treated with an equal volume of buffer A/100 mM NaCl supplemented with 1 mg/mL BSA, 0.2 mg/mL tRNA and 0.2 mg/mL salmon testes DNA for 1 hour at 4° C. The beads were then rinsed with 5 volumes of buffer A/100 mM NaCl.

Oligo 5, an antisense DNA oligonucleotide [National Biosciences, Inc., Plymouth, Minn.] covering nucleotides 407–436 of the human telomerase RNA was designed with the sequence 5'-*G CCG AGT CCT GGG TGC ACG TCC CAT AGC TC-3' [where *G is biotinylated] [SEQ ID NO:3]. Oligo 5 was resuspended at a concentration of 100 μM for use in subsequent experiments.

140 μl of pooled heparin material at a protein concentration of 9 mg/mL was supplemented with 1.6 mM Oligo 5, 2 mM dTTP, 0.1 mM dATP, 2 mM dGTP, 50 mM Tris HCl pH 7.5, 1 mM Spermidine, 5 mM β-mercaptoethanol, 1 mM $MgCl_2$, 50 mM Potassium Acetate, 1 mM EGTA and incubated at 30° C. for 1 hour. The reaction mixture was added to 400 μl of pre-treated NeutrAvidin beads and mixed at 4° C. for 1–4 hour(s).

The slurry was then poured into a small disposable column and the flow-through was drained off. The flow-through was put back through the column up to three times. The column was then washed with at least 4 column volumes of buffer A/100 mM NaCl and eluted with buffer A/500 mM NaCl. Fractions were tested for telomerase activity by primer elongation assay.

Figure 6:
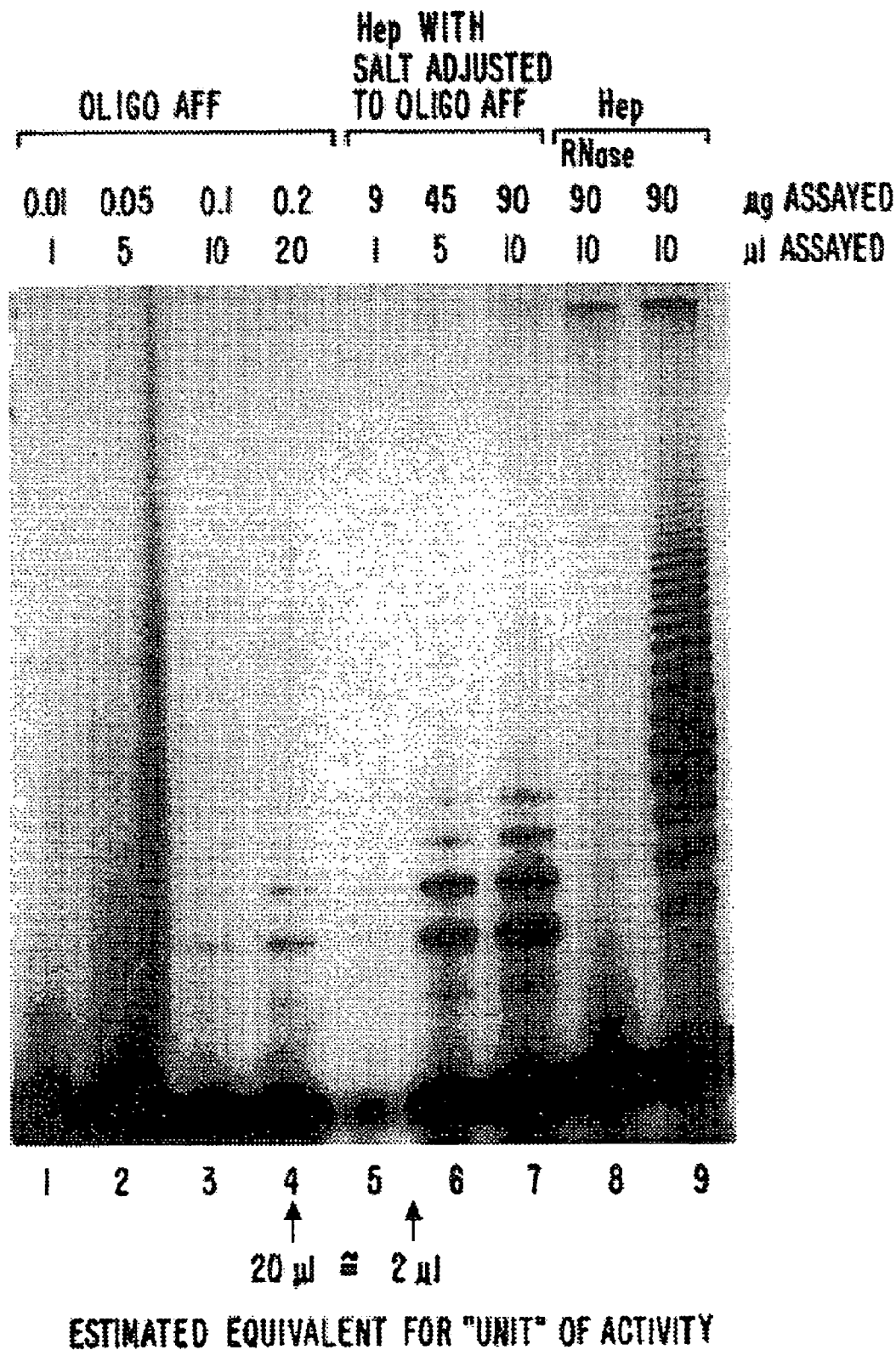
FIG. 6 shows the results of a primer elongation assay from a telomerase preparation from the Oligo 5 affinity isolation active pool (lanes 1–4), the POROS® Heparin 20 HE-1 chromatography active pool adjusted to the salt concentration used for affinity isolation (lanes 5–7), and the POROS® Heparin 20 HE-1 active pool (lanes 8 and 9) in the four-step purification procedure.

The relative specific activity of telomerase for these two preparations was determined exactly as described above for the previous steps with one exception. Telomerase is released from the POROS® 50 HQ, the POROS® Heparin HE-1, and the oligo 5 affinity columns in purification steps 2, 3, and 4 by increasing the salt concentration in the wash buffer. Since salt concentrations over 100 mM inhibit telomerase activity (FIG. 6, compare lanes 7 and 9), the active pools from purification steps 2 and 3 were dialyzed to lower the salt concentration to that of the preparation loaded onto the column for those steps. In purification step 4 (oligo 5 affinity), the pool of active fractions was not desalted. To determine an accurate relative activity, the salt concentration of the preparation loaded onto the affinity column (POROS® Heparin 20 HE-1 active pool) was adjusted to be the same as the Oligo 5 affinity active pool.

Titrations of the two preparations in the primer elongation assay are shown in FIG. 6; measured and calculated values are shown in Table 4. These data indicate that the human telomerase in the Oligo 5 active pool is 90-fold purified compared to that in the POROS® Heparin 20 HE-1 active pool. The cumulative purification after this fourth step is 90×6.8×5.8=3,550. Hence, the human telomerase made by this method has 3,550-fold increased relative purity compared to that in the CHAPS S-100 extract. The yield of the affinity chromatography step is 29% for telomerase activity; the cumulative yield of telomerase activity for this method is 14%.

EXAMPLE IV

Five Step Method for Purifying Telomerase

A method of making human telomerase that has 32,660-fold increased relative purity compared to that in crude cell extracts is described. This method comprises five steps in succession: 1) CHAPS detergent S-100 extract preparation from 293 cells; 2) chromatography of the S-100 extract on POROS® 50 HQ matrix; 3) chromatography of the POROS® 50 HQ active fractions on POROS® Heparin 20 HE-1 matrix; 4) chromatography of the POROS® Heparin 20 HE-1 active fractions on POROS® spermidine matrix; and 5) chromatography of the POROS® spermidine active fractions on oligonucleotide 5 affinity matrix. Protocols are provided for preparation of the spermidine matrix and running of the spermidine column. Protocols for all other steps were provided in the 4-step method of Example III.

In the 5-step method, the first three steps are the same as in the 4-step method. In the fourth step, 0.7 mL of a POROS® Heparin 20 HE-1 active pool was subjected to chromatography on a freshly prepared (i.e., not commercially available) POROS® spermidine column, and fractions containing telomerase activity were combined for a total active pool of 0.15 mL. Chromatography was performed as follows.

POROS®-Spermidine was prepared in the following manner. Dried POROS® 20 EP (Perspective 1-6129-03) was placed in coupling buffer (0.1 M sodium phosphate adjusted to pH 10.0 with KOH) to allow beads to hydrate. The hydrated beads were transferred to a disposable column and rinsed with coupling buffer for 20 bed volume. Two bed volumes of a 0.2 M spermidine tetrahydrochloride (Sigma) –0.1 M sodium phosphate were added. The solution of spermidine-coupling buffer was re-adjust to pH 10. (20 mL of 0.1 M sodium phosphate-0.22 M Spermidine+1.5 mL of 1 N NaOH=0.2 M spermidine-0.1 M sodium phosphate pH 10.0). The beads were rotated with the spermidine solution overnight at room temperature. The spermidine solution was washed off with 20 bed volume of coupling buffer. The remaining reactive groups of the POROS® 20 EP beads were quenched with 2 bed volume of 0.1 M ethanolamine made up in coupling buffer. The mixture was rotated for 2 hours at room temperature. The mixture was washed with 20 bed volumes of coupling buffer. The mixture was washed with 10 bed volume of buffer A/100 mM NaCl and packed into columns for chromatography.

Figure 7:
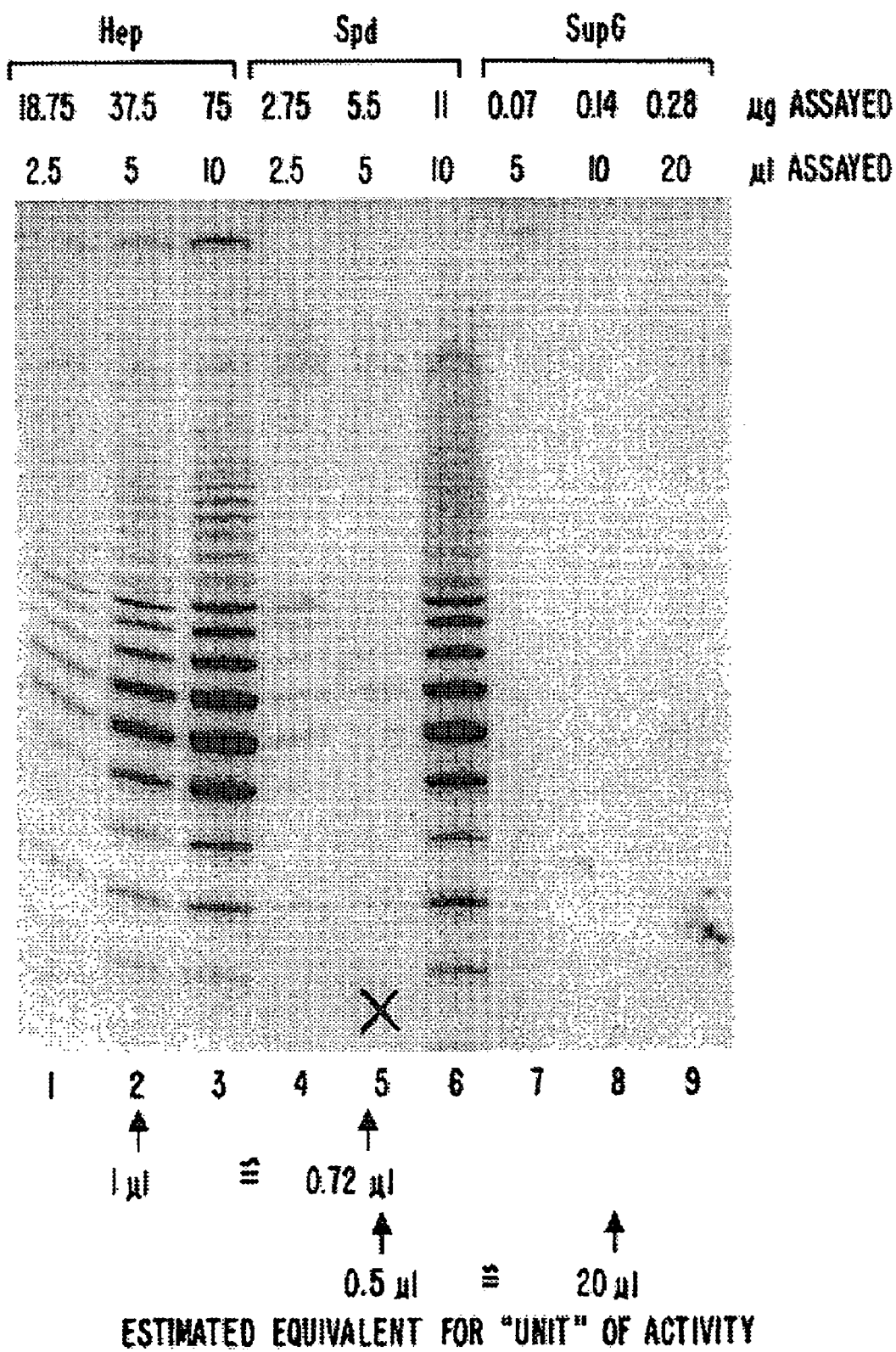
FIG. 7 shows the results of a primer elongation assay from telomerase preparations from the POROS® Heparin 20 HE-1 chromatography active pool (lanes 1–3) and the POROS® Spermidine chromatography active pool (lanes 4–6) in the five-step purification procedure, and from the Superose® 6 active pool (lanes 7–9) in the six-step assay.

The POROS®-Spermidine column was equilibrated at 4° C. with 10 column volume (CV) of buffer A/100 mM NaCl prior to the application of the sample. The sample POROS® Heparin 20 HE-1 active pool was dialyzed in buffer A to or below 100 mM NaCl) is applied to the column and chromatographed at a flow rate of 0.6 CV per minute. The column was then washed at the same flow rate with 5 CV of buffer A/100 mM NaCl. The proteins were eluted at the same flow rate with the following steps:

3 CV of buffer A 100 mM KCl-90 mM NaCl
  3 CV of buffer A 150 mM KCl-85 mM NaCl
  3 CV of buffer A 200 mM KCl-80 mM NaCl
  3 CV of buffer A 1000 mM KCl Proteins were eluted at each step, telomerase being essentially eluted from the POROS®-Spermidine column with buffer A/150 mM KCl-85 mM NaCl. The relative specific activity of telomerase for these two preparations was determined. Titrations of the two preparations in the primer elongation assay are shown in FIG. 7; measured and calculated values are shown in Table 5. These data indicate that the human telomerase in the POROS® spermidine active pool is 9.2-fold purified compared to that in the POROS® Heparin 20 HE-1 active pool. The cumulative purification after this fourth step is 9.2×6.8×5.8=363-fold purified compared to the CHAPS S-100 extract. The yield of the POROS® spermidine chromatography is 30% for telomerase activity, and the cumulative yield after these four steps is 14.6%.

Oligo 5 affinity chromatography of POROS® spermidine active fractions purifies human telomerase by a factor of 90 with 29% yield (as it did with POROS® Heparin 20 HE-1 active fractions). Thus, this 5-step method would produce human telomerase that has 90×363=32,660-fold increased relative purity compared to that in CHAPS S-100 extracts. The yield of this 5-step method is 4.2%

EXAMPLE V

Six Step Method for Purifying Telomerase

A method of making human telomerase that is 65,320-fold purified compared to that in crude cell extracts is described. This method comprises six steps in succession: 1) CHAPS detergent S-100 extract preparation from 293 cells; 2) chromatography of the s-100 extract on POROS® 50 HQ matrix; 3) chromatography of the POROS® 50 HQ active fractions on POROS® Heparin 20 HE-1 matrix; 4) chromatography of the POROS® Heparin 20 HE-1 active fractions on POROS® spermidine matrix; 5) chromatography of the POROS® Spermidine active fractions on Superose® 6 sizing column; and 6) chromatography of the Superose® 6 sizing column active fractions on Oligo 5 affinity matrix. A protocol for running the Superose® column is provided. Protocols for all other steps were provided previously.

In the 6-step method, the first four steps are the same as in the 5-step method. In the fifth step, 0.02 mL of material from the POROS® spermidine active pool collected in Example IV was subjected to chromatography on a Superose 6 sizing column, and the fractions containing telomerase activity were combined for a total active pool of 0.16 mL. Superose® 6 chromatography was performed as follows.

The 2.4 mL Superose® 6, PC 3.2/30 column from Pharmacia is pre-equilibrated with 2 CV of buffer A/150 mM NaCl at a flow rate of 40 µl/min. For each Superose 6 run, 20 µl of active POROS® spermidine fraction is loaded on the column which is run at a flow rate of 20 µl/min in buffer A/150 mM NaCl. The bulk of $OD_{280}$ absorbing protein elutes from the column between 1.00 mL and 1.4 mL. The peak of telomerase activity is eluted between 1.4 and 1.6 mL, on the trailing end of the peak of proteins.

The relative specific activity of telomerase for these two preparations was determined. Titrations of the two preparations in the primer elongation assay are shown in FIG. 7; measured and calculated values are shown in Table 5. These data indicate that the human telomerase in the Superose® 6 active pool is 2-fold increased purified compared to that in the POROS® spermidine active pool. The cumulative purification after this fifth step is 2×9.2×6.8×5.8=725.7-fold relative purity compared to the CHAPS S-100 extract. The yield of the Superose® 6 chromatography is 20% for telomerase activity, and the cumulative yield after these five steps is 2.9%.

Oligo 5 affinity chromatography of Superose® 6 active fractions may purify human telomerase to the same extent as for POROS® Heparin 20 HE-1 active fractions. Thus, this 6-step method would produce human telomerase that is 90×725.7=65,320-fold purified compared to that in CHAPS S-100 extracts. The yield of this 6-step method is 0.85%.

The present invention provides substantially novel means and methods for preparing purified telomerase. While examples have been provided, the above description is illustrative and not restrictive. Many variations of the invention will become apparent to those persons skilled in the art upon review of this specification. The scope of the invention should, therefore, be determined not with reference to the above description, but instead should be determined with reference to the appended claims along with their full scope of equivalents.

TABLE 4

PURIFICATION TABLE FOR 4 STEP METHOD

| Step | | Vol. | Prot. Conc. | Total Prot. | µl per "unit activity" | Total Units | Sp. Act. Units/µg | Purification Step | Purification Cum. | Yield Step | Yield Cum. |
|---|---|---|---|---|---|---|---|---|---|---|---|
| 1 | CHAPS S-100 ↓ | 883 mL | 7.7 mg/mL | 6799.1 mg | 20 µl | 44,150 | 0.0065 | 1 | 1 | 100% | 100% |

TABLE 4-continued

PURIFICATION TABLE FOR 4 STEP METHOD

| Step | | Vol. | Prot. Conc. | Total Prot. | µl per "unit activity" | Total Units | Sp. Act. Units/µg | Purification Step | Purification Cum. | Yield Step | Yield Cum. |
|---|---|---|---|---|---|---|---|---|---|---|---|
| 2 | HQ | 72 mL | 10.7 mg/mL | 770.4 mg | 2.5 µl | 28,800 | 0.037 | 5.8x | 5.8x | 65% | 65% |
|   |    | 24 mL | 6.1 mg/mL | 146.4 mg | 7.5 µl | 3200 | 0.0219 | | | | |
| ↓ | | | | | | | | | | | |
| 3 | Hep | 6 mL | 2.7 mg/mL | 16.2 mg | 2.5 µl | 2400 | 0.148 | 6.8x | 39.4x | 75% | 48.8% |
|   |     | 140 µl | 9 mg/mL | 1260 µg | 2 µl | 70 | 0.056 | | | | |
| ↓ | | | | | | | | | | | |
| 4 | Oligo 5 Affin | 400 µl | 0.01 mg/mL | 4 µg | 20 µl | 20 | 5 | 90x | 3,550x | 29% | 14% |

TABLE 5

PURIFICATION BY POROS ® SPERMIDINE AND Superose ® 6

| | vol. | prot. conc. | total prot. | µl per unit activity | total units | sp. act. units/µg | purification | yield |
|---|---|---|---|---|---|---|---|---|
| Hep | 700 µl | 7.5 mg/mL | 5250 µg | 1 µl | 700 u | 0.133 | | |
| Spd | 150 µl | 1.13 mg/mL | 169.5 µg | 0.72 µl | 208.3 u | 1.23 | 9.2x | 30% |
|     | 20 µl | 1.1 mg/mL | 22 µg | 0.5 µl | 40 u | 1.82 | | |
| Sup6 | 160 µl | 0.014 mg/mL | 2.24 µg | 20 µl | 8 u | 3.57 | 2x | 20% |

---

The invention claimed is:

1. A method for producing a compound that regulates telomerase activity, comprising:
   a) obtaining a preparation of mammalian telomerase enzyme that is at least ~2000-fold more pure than an extract of cells from adenovirus-transformed kidney cell line (293 cells), wherein the telomerase enzyme contains telomerase RNA component, and has a molecular weight of 200–2000 kDa;
   b) combining the preparation with a test compound;
   c) determining telomerase activity of the enzyme in the presence of the test compound;
   d) identifying the compound as being a regulator of telomerase if the telomerase activity measured in step c) is affected by the presence of the compound; and then
   e) producing the compound if it is identified as being a regulator of telomerase in step d).

2. A method for producing a compound that regulates telomerase activity, comprising:
   a) identifying the compound as being a regulator of telomerase; and then
   b) producing the compound if it is identified as being a regulator of telomerase in step a);
   wherein the compound has been identified as a regulator of telomerase by a process comprising:
   i) obtaining a preparation of mammalian telomerase enzyme that is at least ~2000-fold more pure than an extract of cells from adenovirus-transformed kidney cell line (293 cells), wherein the telomerase enzyme contains telomerase RNA component, and has a molecular weight of 200–2000 kDa;
   ii) combining the preparation with a test compound;
   iii) determining telomerase activity of the enzyme in the presence of the test compound;
   iv) identifying the compound as being a regulator of telomerase if the telomerase activity measured in step iii) is affected by the presence of the compound.

3. The method of claim 1 or claim 2, wherein the telomerase preparation was obtained by a process in which a solution containing telomerase activity was combined with an oligonucleotide having specific activity for mammalian telomerase; and then protein was collected that had bound the oligonucleotide.

4. The method of claim 3, wherein the oligonucleotide comprises a retrievable label such as biotin.

5. The method of claim 3, wherein the solution that was combined with the oligonucleotide had been obtained by preparing an enriched solution from a cell expressing telomerase, whereby telomerase enzyme in the enriched solution was separated from other proteins expressed by the cell.

6. The method of claim 1 or claim 2, wherein the process used to prepare the telomerase comprised combining a fraction containing telomerase enzyme with an anion exchange matrix, and collecting protein that bound the matrix.

7. The method of claim 1 or claim 2, wherein the process used to prepare the telomerase comprised combining a fraction containing telomerase enzyme with a cation exchange matrix (such as a heparin matrix), and collecting protein that bound the matrix.

8. The method of claim 1 or claim 2, wherein the process used to prepare the telomerase comprised combining a fraction containing telomerase enzyme with an intermediate selectivity matrix, and collecting protein that bound the matrix; wherein the intermediate selectivity matrix had at least one of the following substituents: hydroxyapatite, a polyamine (such as spermine or spermidine), poly guanylic acid, a divalent metal ion (such as $Ni^{++}$), a positively charged poly-amino acid (such as poly-L-lysine), a positively charged enzyme (such as histone), or aminophenylboronic acid.

9. The method of claim 1 or claim 2, wherein the process used to prepare the telomerase comprised separating a fraction containing the telomerase enzyme by gel filtration chromatography or gradient centrifugation that separates molecules >200 kDa.

10. The method of claim 3, wherein the oligonucleotide contains a sequence that binds specifically to telomerase RNA component.

11. The method of claim 10, wherein the oligonucleotide contains the sequence of oligo 5 (SEQ. ID NO:3).

12. The method of claim 3, wherein the oligonucleotide contains a sequence that is specifically recognized by telomerase protein.

13. The method of claim 12, wherein the oligonucleotide contains the sequence $(TTAGGG)_3$ (SEQ. ID NO:6).

14. The method of claim 12, wherein the oligonucleotide does not contain the sequence $(TTAGGG)_3$ (SEQ. ID NO:6).

15. The method of claim 12, wherein the oligonucleotide contains the sequence of M2/TS (SEQ. ID NO:8).

16. The method of claim 12, wherein the telomerase preparation is at least ~20,000 fold more pure than the cell extract.

17. The method of claim 1 or claim 2, wherein the telomerase preparation is between ~3,000 and ~60,000 fold more pure than the cell extract.

18. The method of claim 1 or claim 2, wherein the telomerase protein is human.

19. The method of claim 1 or claim 2, wherein the telomerase preparation has measurable telomerase activity in 0.2 μg of protein when quantified in a telomere primer elongation assay in which $^{32}P$-labeled primer extensions are separated on a gel and detected using a phosphoimager screen.

20. The method of claim 1 or claim 2, wherein the telomerase enzyme is present in the preparation at a concentration of at least $3\times10^{10}$ mol $L^{-1}$.

21. The method of claim 1 or claim 2, wherein the telomerase enzyme is present in the preparation at a concentration of at least $2\times10^{-9}$ mol $L^{-1}$.

22. The method of claim 1 or claim 2, wherein the telomerase activity is determined by a primer elongation assay.

23. The method of claim 1 or claim 2, wherein the telomerase activity is determined in by a dot blot assay.

24. The method of claim 1 or claim 2, whereby the compound is identified as being an inhibitor of telomerase.

25. The method of claim 1 or claim 2, whereby the compound is identified as being an activator of telomerase.

* * * * *